(12) United States Patent
Ghadimi et al.

(10) Patent No.: US 11,857,288 B2
(45) Date of Patent: Jan. 2, 2024

(54) SYSTEMS AND METHODS FOR PHASE UNWRAPPING FOR DENSE MRI USING DEEP LEARNING

(71) Applicant: University of Virginia Patent Foundation, Charlottesville, VA (US)

(72) Inventors: Sona Ghadimi, Charlottesville, VA (US); Changyu Sun, Charlottesville, VA (US); Xue Feng, Zion Crossroads, VA (US); Craig H. Meyer, Charlottesville, VA (US); Frederick H. Epstein, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 351 days.

(21) Appl. No.: 17/166,604

(22) Filed: Feb. 3, 2021

(65) Prior Publication Data
US 2021/0267455 A1 Sep. 2, 2021

Related U.S. Application Data

(60) Provisional application No. 62/969,342, filed on Feb. 3, 2020.

(51) Int. Cl.
*G06T 7/00* (2017.01)
*A61B 5/00* (2006.01)
(Continued)

(52) U.S. Cl.
CPC ........ *A61B 5/0044* (2013.01); *A61B 5/02028* (2013.01); *A61B 5/7267* (2013.01);
(Continued)

(58) Field of Classification Search
CPC . A61B 5/0044; A61B 5/02028; A61B 5/7267; A61B 5/7278; A61B 5/055;
(Continued)

(56) References Cited

U.S. PATENT DOCUMENTS 10,335,037 B2 * 7/2019 Jolly .......................... G06T 7/13
10,524,687 B2 * 1/2020 Osman ................. A61B 5/7207
(Continued)

OTHER PUBLICATIONS

Abadi, M. et al. TensorFlow: Large-Scale Machine Learning on Heterogeneous Distributed Systems. *CoRR* abs/1603.0, (2016).
(Continued)

*Primary Examiner* — Van D Huynh
(74) *Attorney, Agent, or Firm* — Meunier Carlin & Curfman LLC

(57) ABSTRACT

A method of cardiac strain analysis uses displacement encoded magnetic resonance image (MRI) data of a heart of the subject and includes generating a phase image for each frame of the displacement encoded MRI data. Phase images include potentially phase-wrapped measured phase values corresponding to pixels of the frame. A convolutional neural network CNN computes a wrapping label map for the phase image, and the wrapping label map includes a respective number of phase wrap cycles present at each pixel in the phase image. Computing an unwrapped phase image includes adding a respective phase correction to each of the potentially-wrapped measured phase values of the phase image, and the phase correction is based on the number of phase wrap cycles present at each pixel. Computing myocardial strain follows by using the unwrapped phase image for strain analysis of the subject.

17 Claims, 18 Drawing Sheets

(51) Int. Cl.

| | |
|---|---|
| *A61B 5/02* | (2006.01) |
| *G06T 7/11* | (2017.01) |
| *G16H 30/40* | (2018.01) |
| *G06N 3/08* | (2023.01) |
| *G01R 33/56* | (2006.01) |
| *A61B 5/055* | (2006.01) |

(52) U.S. Cl.
CPC ............ *A61B 5/7278* (2013.01); *G01R 33/56* (2013.01); *G06N 3/08* (2013.01); *G06T 7/0012* (2013.01); *G06T 7/11* (2017.01); *G16H 30/40* (2018.01); *A61B 5/055* (2013.01); *A61B 2576/023* (2013.01); *G06T 2207/10088* (2013.01); *G06T 2207/20081* (2013.01); *G06T 2207/20084* (2013.01); *G06T 2207/30048* (2013.01)

(58) Field of Classification Search
CPC .............. A61B 2576/023; G01R 33/56; G01R 33/5608; G01R 33/56313; G01R 33/56545; G01R 33/56325; G06N 3/08; G06N 3/045; G06T 7/0012; G06T 7/11; G06T 2207/10088; G06T 2207/20081; G06T 2207/20084; G06T 2207/30048; G16H 30/40; G16H 30/20; G16H 50/20; G16H 50/70
See application file for complete search history.

(56) References Cited

U.S. PATENT DOCUMENTS

| | | | | |
|---|---|---|---|---|
| 2008/0015428 | A1* | 1/2008 | Epstein | .................... G06T 7/215 600/410 |
| 2018/0116521 | A1* | 5/2018 | Kar | .......................... G16H 30/40 |
| 2018/0203087 | A1* | 7/2018 | Ye | ........................ G01R 33/443 |
| 2019/0279361 | A1 | 9/2019 | Meyer et al. | |
| 2019/0302210 | A1* | 10/2019 | Epstein | ............. G01R 33/56325 |
| 2019/0302211 | A1* | 10/2019 | Cai | ........................ G06T 11/008 |
| 2020/0300955 | A1* | 9/2020 | Sandino | ............. G01R 33/5608 |

OTHER PUBLICATIONS

Aletras, A. H., Ding, S., Balaban, R. S. & Wen, H. Dense: displacement encoding with stimulated echoes in cardiac functional MRI. *J. Magn. Reson.* 137, 247-252 (1999).
Auger, D.A., Cai, X., Sun, Ch., Epstein, F. H. Improved phase unwrapping algorithm for automatic cine DENSE strain analysis using phase predictions and region growing. in *SMRT 27th Annual Meeting* (2018). Abstract #0767.
Bai, W. et al. Automated cardiovascular magnetic resonance image analysis with fully convolutional networks. *J. Cardiovasc. Magn. Reson.* 20, 65 (2018).
Bilchick, K. C. et al. CMR DENSE and the Seattle Heart Failure Model Inform Survival and Arrhythmia Risk After CRT. *JACC. Cardiovasc. Imaging* 13, 924-936 (2020).
Bilchick, K. C. et al. Impact of mechanical activation, scar, and electrical timing on cardiac resynchronization therapy response and clinical outcomes. *J. Am. Coll. Cardiol.* 63, 1657-1666 (2014).
Bratt, A. et al. Machine learning derived segmentation of phase velocity encoded cardiovascular magnetic resonance for fully automated aortic flow quantification. *J. Cardiovasc. Magn. Reson.* 21, 1 (2019).
Cerqueira, M. D. et al. Standardized myocardial segmentation and nomenclature for tomographic imaging of the heart. *J. Cardiovasc. Magn. Reson.* 4, 203-210 (2002).
Chen, X. et al. Accelerated two-dimensional cine DENSE cardiovascular magnetic resonance using compressed sensing and parallel imaging. *J. Cardiovasc. Magn. Reson.* 18, 38 (2016).
Chen, X., Salerno, M., Yang, Y. & Epstein, F. H. Motion-compensated compressed sensing for dynamic contrast-enhanced MRI using regional spatiotemporal sparsity and region tracking: block low-rank sparsity with motion-guidance (BLOSM). *Magn. Reson. Med.* 72, 1028-1038 (2014).
D'Errico, J. Surface Fitting using gridfit. *MATLAB Central File Exchange* vol. 1 1-6. http://uk.mathworks.com/matlabcentral/fileexchange/8998-surface-fitting-using-gridfit (2020).
Dardikman-Yoffe, G. et al. PhUn-Net: ready-to-use neural network for unwrapping quantitative phase images of biological cells. *Biomed. Opt. Express* 11, 1107-1121 (2020).
Duan, J. et al. Automatic 3D Bi-Ventricular Segmentation of Cardiac Images by a Shape-Refined Multi-Task Deep Learning Approach. *IEEE Trans. Med. Imaging* 38, 2151-2164 (2019).
Ernande, L. et al. Systolic myocardial dysfunction in patients with type 2 diabetes mellitus: Identification at MR imaging with cine displacement encoding with stimulated echoes. *Radiology* 265, 402-409 (2012).
Fahmy, A. S. et al. Three-dimensional Deep Convolutional Neural Networks for Automated Myocardial Scar Quantification in Hypertrophic Cardiomyopathy: A Multicenter Multivendor Study. *Radiology* 294, 52-60 (2019).
Fahmy, A. S., El-Rewaidy, H., Nezafat, M., Nakamori, S. & Nezafat, R. Automated analysis of cardiovascular magnetic resonance myocardial native T1 mapping images using fully convolutional neural networks. *J. Cardiovasc. Magn. Reson.* 21, 7 (2019).
Feng, X., Kramer, Chirstopher M., Meyer, C. H. View-independent cardiac MRI segmentation with rotation-based training and testing augmentation using a dilated convolutional neural network. in *ISMRM 27th Annual Meeting* (2019), 2140.
Feng, X., Qing, K., Tustison, N. J., Meyer, C. H. & Chen, Q. Deep convolutional neural network for segmentation of thoracic organs-at-risk using cropped 3D images. *Med. Phys.* 46, 2169-2180 (2019).
Ferdian, E. et al. Fully Automated Myocardial Strain Estimation from Cardiovascular MRI-tagged Images Using a Deep Learning Framework in the UK Biobank. *Radiol. Cardiothorac. Imaging* 2, e190032 (2020).
Gilliam, A.D., Suever, J. D. DENSEanalysis: Cine DENSE Processing Software. https://github.com/denseanalysis/denseanalysis.
Hammouda, K. et al. A New Framework for Performing Cardiac Strain Analysis from Cine MRI Imaging in Mice. *Sci. Rep.* 10, 7725 (2020).
Intro to Phase-encoding—I "I understand frequency-encoding, but I just don't get phase-encoding. Can you explain?" 2021. 2 pages. Available on-line: http://mriquestions.com/what-is-phase-encoding.html.
Jing, L. et al. Cardiac remodeling and dysfunction in childhood obesity: a cardiovascular magnetic resonance study. *J. Cardiovasc. Magn. Reson.* 18, 28 (2016).
Kim, D., Gilson, W. D., Kramer, C. M. & Epstein, F. H. Myocardial tissue tracking with two-dimensional cine displacement-encoded MR imaging: development and initial evaluation. *Radiology* 230, 862-871 (2004).
Lee, A. T., Bruce Pike, G. & Pelc, N. J. Three—Point Phase—Contrast Velocity Measurements with Increased Velocity-to-Noise Ratio. *Magn. Reson. Med.* 33, 122-126 (1995).
Lin, K. et al. Reproducibility of cine displacement encoding with stimulated echoes (DENSE) in human subjects. *Magn. Reson. Imaging* 35, 148-153 (2017).
Mangion, K. et al. Circumferential Strain Predicts Major Adverse Cardiovascular Events Following an Acute ST-Segment-Elevation Myocardial Infarction. *Radiology* 290, 329-337 (2019).
Puyol-Anton, E. et al. Fully automated myocardial strain estimation from cine MRI using convolutional neural networks. in *2018 IEEE 15th International Symposium on Biomedical Imaging, ISBI 2018* vols. Apr. 2018 1139-1143 (IEEE Computer Society, 2018).
Ronneberger, O., Fischer, P. & Brox, T. U-Net: Convolutional Networks for Biomedical Image Segmentation. in *MICCAI* (2015).
Ruijsink, B. et al. Fully Automated, Quality-Controlled Cardiac Analysis From CMR: Validation and Large-Scale Application to Characterize Cardiac Function. *JACC Cardiovasc. Imaging* 13, 684-695 (2020).
Spoorthi, G. E., Gorthi, S. & Gorthi, R. K. PhaseNet: A Deep Convolutional Neural Network for Two-Dimensional Phase Unwrapping. *IEEE Signal Process. Lett.* 26, 54-58 (2019).

(56) References Cited

OTHER PUBLICATIONS

Spottiswoode, B. S. et al. Motion-guided segmentation for cine DENSE MRI. *Med. Image Anal.* 13, 105-115 (2009).

Spottiswoode, B. S. et al. Tracking myocardial motion from cine DENSE images using spatiotemporal phase unwrapping and temporal fitting. *IEEE Trans. Med. Imaging* 26, 15-30 (2007).

Suever, J. D. et al. Simplified post processing of cine DENSE cardiovascular magnetic resonance for quantification of cardiac mechanics. *J. Cardiovasc. Magn. Reson.* 16, 94 (2014).

Szymanski, C., Lévy, F. & Tribouilloy, C. Should LVEF be replaced by global longitudinal strain? *Heart* 100, 1655 LP—1656 (2014).

Tan, L. K., McLaughlin, R. A., Lim, E., Abdul Aziz, Y. F. & Liew, Y. M. Fully automated segmentation of the left ventricle in cine cardiac MRI using neural network regression. *J. Magn. Reson. Imaging* 48, 140-152 (2018).

Tao, Q. et al. Deep Learning-based Method for Fully Automatic Quantification of Left Ventricle Function from Cine MR Images: A Multivendor, Multicenter Study. *Radiology* 290, 81-88 (2019).

Tayal, U. et al. The feasibility of a novel limited field of view spiral cine DENSE sequence to assess myocardial strain in dilated cardiomyopathy. *Magn. Reson. Mater. Physics, Biol. Med.* 32, 317-329 (2019).

Verzhbinsky, I. A. et al. Estimating Aggregate Cardiomyocyte Strain Using In Vivo Diffusion and Displacement Encoded MRI. *IEEE Trans. Med. Imaging* 39, 656-667 (2020).

Wang, K., Li, Y., Kemao, Q., Di, J. & Zhao, J. One-step robust deep learning phase unwrapping. *Opt. Express* 27, 15100-15115 (2019).

Yin, W. et al. Temporal phase unwrapping using deep learning. *Sci. Rep.* 9, 20175 (2019).

Young, A. A., Li, B., Kirton, R. S. & Cowan, B. R. Generalized spatiotemporal myocardial strain analysis for DENSE and SPAMM imaging. *Magn. Reson. Med.* 67, 1590-1599 (2012).

Zhang, J., Tian, X., Shao, J., Luo, H. & Liang, R. Phase unwrapping in optical metrology via denoised and convolutional segmentation networks. *Opt. Express* 27, 14903-14912 (2019).

Zhang, T. et al. Rapid and robust two-dimensional phase unwrapping via deep learning. *Opt. Express* 27, 23173-23185 (2019).

Zheng, Q., Delingette, H., Duchateau, N. & Ayache, N. 3-D Consistent and Robust Segmentation of Cardiac Images by Deep Learning With Spatial Propagation. *IEEE Trans. Med. Imaging* 37, 2137-2148 (2018).

Zhong, X., Helm, P. A. & Epstein, F. H. Balanced multipoint displacement encoding for DENSE MRI. *Magn. Reson. Med.* 61, 981-988 (2009).

Zhong, X., Spottiswoode, B. S., Meyer, C. H., Kramer, C. M. & Epstein, F. H. Imaging three-dimensional myocardial mechanics using navigator-gated volumetric spiral cine DENSE MRI. *Magn. Reson. Med.* 64, 1089-1097 (2010).

Zou, K. H. et al. Statistical validation of image segmentation quality based on a spatial overlap index. *Acad. Radiol.* 11, 178-189 (2004).

\* cited by examiner

| Class | $k_{ij}$ | Label |
|---|---|---|
| 1- No wrap | 0 | 0 |
| 2- Wrapped myocardium (-2π) | -1 | 1 |
| 3- Wrapped myocardium (+2π) | +1 | 2 |

*FIG. 3*

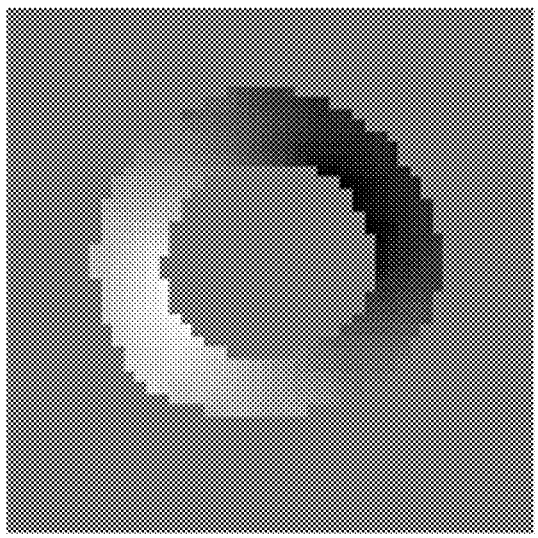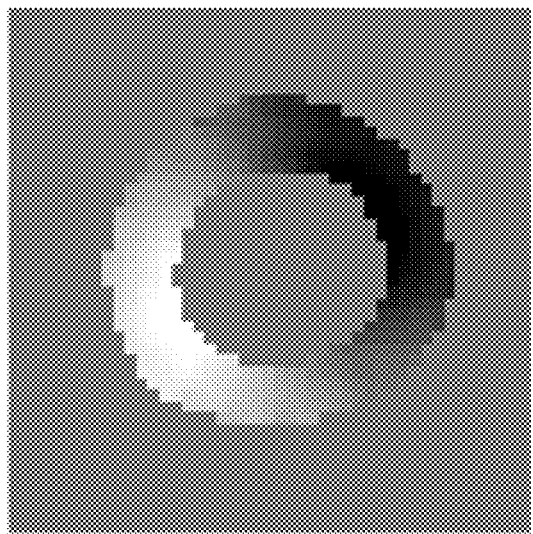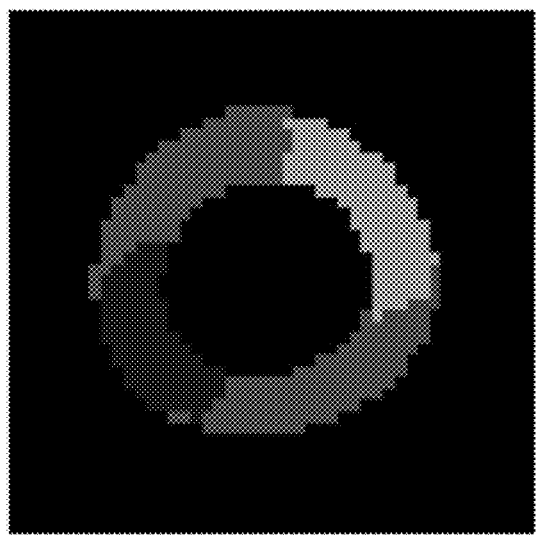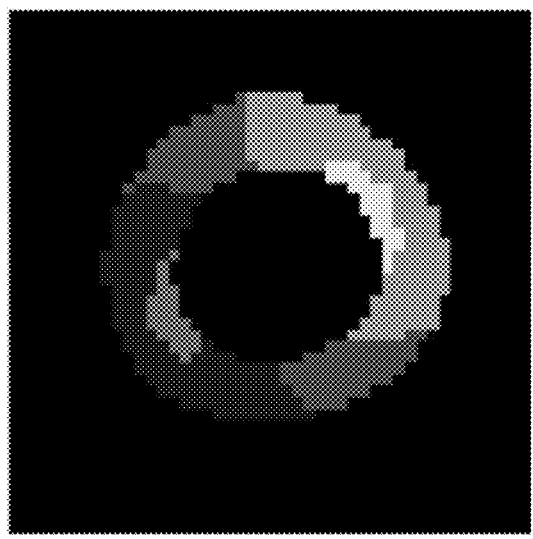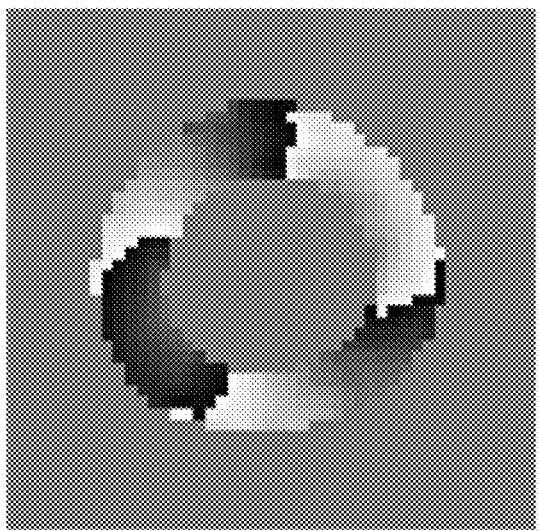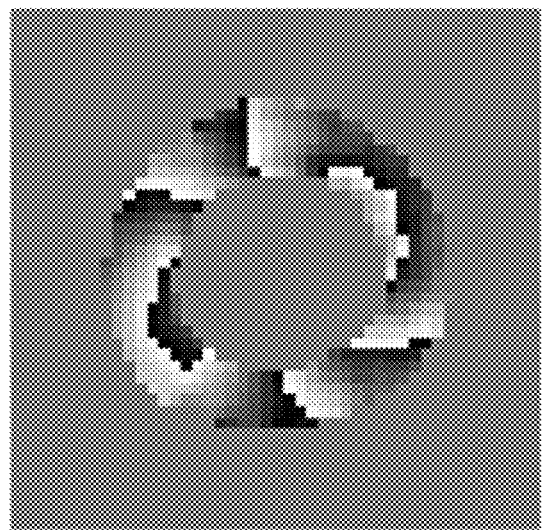
*FIG. 7C*
*FIG. 7B*
*FIG. 7A*

|  | | MSE |
|---|---|---|
| Typical SNR | U-Net | 0.1±0.2 |
|  | Path-following | 0.08±0.08 |
| Low SNR | U-Net | 0.07±0.09* |
|  | Path-following | 0.22±0.49 |

FIG. 9

|  | segment 1 | segment 2 | segment 3 | segment 4 | segment 5 | segment 6 |
| --- | --- | --- | --- | --- | --- | --- |
| mean $E_{xx}$ (user-assisted) | -0.13±0.06 | -0.12±0.05 | -0.15±0.07 | -0.16±0.09 | -0.15±0.07 | -0.15±0.06 |
| mean $E_{xx}$ (automated DL) | -0.13±0.06 | -0.12±0.06 | -0.15±0.07 | -0.16±0.09 | -0.16±0.08 | -0.15±0.06 |
| variance of $E_{xx}$ (user-assisted) | 1E-4±1E-4 | 6E-4±8E-4 | 1E-3±2E-3 | 9E-4±7E-4 | 5E-4±5E-4 | 8E-4±1E-3 |
| variance of $E_{xx}$ (automated DL) | 3E-4±3E-4 | 6E-4±5E-4 | 1E-3±2E-3 | 1E-3±1E-3 | 5E-4±3E-4 | 8E-4±1E-3 |

*FIG. 12*

SYSTEMS AND METHODS FOR PHASE UNWRAPPING FOR DENSE MRI USING DEEP LEARNING

CROSS-REFERENCE TO RELATED APPLICATIONS

This application claims priority to and the benefit of U.S. provisional patent application No. 62/969,342, filed on Feb. 3, 2020, and titled "System and Method for Phase Unwrapping for DENSE MRI using Deep Learning", the disclosure of which is hereby incorporated by reference herein in its entirety.

STATEMENT OF GOVERNMENT RIGHTS

This invention was made with government support under grant number HL147104 awarded by the National Institutes of Health. The government has certain rights in the invention.

BACKGROUND

Myocardial strain imaging is sensitive and prognostic for the assessment of heart disease, with potential advantages over imaging of ejection fraction (EF)[1]. Among various strain imaging methods, cine displacement encoding with stimulated echoes (DENSE)[2-4] magnetic resonance imaging (MRI) uniquely measures heart motion by encoding myocardial displacement into the signal phase, which can facilitate high measurement accuracy[5], high reproducibility of global and segmental strain[6,7], and rapid computation of displacement and strain[5,8]. These properties translate to benefits in clinical performance. For example, cine DENSE shows superiority over late gadolinium enhanced (LGE) MRI and feature tracking in predicting major adverse cardiac events after myocardial infarction[9] and predicting outcomes of heart failure (HF) patients treated with cardiac resynchronization therapy[10]. Cine DENSE also detects contractile dysfunction in childhood obesity[11] and adult type 2 diabetes even when EF is normal[12].

While low-rank[13,14] and reduced field-of-view[15] methods have been developed recently to accelerate data acquisition for DENSE, there remains a need and opportunity to accelerate DENSE strain analysis and to eliminate all steps that require user assistance. Currently, LV segmentation of DENSE is typically performed using motion-guided segmentation[8], which can require manual segmentation of the LV epicardial and endocardial borders at a single cardiac phase, followed by automated propagation of these borders to all other phases (guided by the measured myocardial displacements). User intervention is sometimes needed to adjust the segmentation results. Identification of the anterior RV insertion point is currently performed manually by a user. Also, phase unwrapping is typically performed using a path-following method[5], and this method requires user selection of seed points placed in regions known to not have phase wrapping.

It is with respect to these and other considerations that the various aspects of the present disclosure as described below are presented.

SUMMARY

In one aspect, the present disclosure relates to a method of strain analysis of a cardiac region of interest of a subject from displacement encoded magnetic resonance image (MRI) data. In one embodiment, the method includes the steps of acquiring displacement encoded MRI data corresponding to the cardiac region of interest of the subject and generating a phase image for each frame of the displacement encoded MRI data, wherein the phase image includes potentially phase-wrapped measured phase values corresponding to pixels of the frame. The method includes training a convolutional neural network (CNN) to compute a wrapping label map for the phase image, wherein the wrapping label map includes a respective number of phase wrap cycles present at each pixel in the phase image, allowing for computing, by the trained CNN, the wrapping label map. Computing an unwrapped phase image includes adding a respective phase correction to each of the potentially-wrapped measured phase values of the phase image, wherein the phase correction is based on the number of phase wrap cycles present at each pixel. Computing myocardial strain follows by using the unwrapped phase image for strain analysis of the subject.

In one embodiment, the strain analysis includes quantification of global and segmental strain associated with the heart of the subject.

In one embodiment, the displacement encoded MRI data corresponds to displacement encoded stimulated echo (DENSE) cine frames of MRI image data.

In one embodiment, a U-Net structured CNN is used to compute the wrapping label map.

In one embodiment, at least one additional CNN is configured for epicardial and endocardial segmentation, and the at least one additional CNN assigns one of three classes to each pixel, wherein the three classes are the blood pool, the myocardium, and the background.

In one embodiment, computing the wrapping label map includes labeling each pixel as belonging to one of three classes, the classes including no-wrap, $-2\pi$ wrapped, and $+2\pi$ wrapped.

In one embodiment, the method includes displaying a visual representation of the phase image according to the respective class and label.

In one embodiment, at least one trained CNN is trained at least in part from augmented test data from previously verified test images produced by phase unwrapping the previously verified test image, multiplying a phase unwrapped verified test image by a constant, and phase wrapping a product test image within a range of $-\pi$ to $+\pi$ to generate a new wrap test image.

In one embodiment, the method further includes using at least one additional CNN to (a) identify the left-ventricular (LV) epicardial and endocardial borders; and (b) identify the interior right ventricular-LV insertion point.

In one embodiment, the method further includes using at least one additional CNN to generate (a) segmentation of the LV myocardium; (b) identification of the anterior right-ventricular (RV) insertion point into the LV; and (c) an unwrapped phase image by unwrapping of the potentially-wrapped displacement encoded phase values of the myocardium.

In one embodiment, the method further includes (d) computing the spatiotemporal displacement field of the unwrapped phase image.

In one embodiment, the potentially-wrapped measured phase values correspond to pixel (i, j) of the frame, and the wrapping label map includes values of respective wrapping constants $k_{ij}$ for each pixel (i, j) in the phase image. The respective phase correction for each pixel (i, j) is computed by multiplying each value $k_{ij}$ by $2\pi$, and the unwrapped phase image is computed by adding the phase correction for each pixel (i, j) to each of the potentially-wrapped measured phase values of the phase image.

In one embodiment, the frames of the displacement encoded MRI data include image frames having displacement encoded data generated with multiple cycles of phase wrapping.

In one embodiment, the method uses the trained CNN to estimate the number of cycles of wrapping corresponding to the phase image during displacement encoding that produced the displacement encoded MRI data.

In one embodiment, the method includes converting the unwrapped phase image to a respective displacement array.

In one aspect, the present disclosure relates to a method of using a convolutional neural network (CNN) to calculate a wrapping label map for unwrapping an array of potentially-wrapped measured phase values from frames of magnetic resonance image (MRI) data. In one embodiment, the method includes calculating a phase image for each frame of the displacement encoded MRI data, the phase image including potentially-wrapped measured phase values corresponding to pixels (i, j) of the frame. The method further includes training the convolutional neural network with augmented test data to label each pixel (i, j) as belonging to one of three classes, wherein the classes include a no-wrap label, a $-2\pi$ label, and a $+2\pi$ label. The method includes storing the respective labels in a wrapping label map.

In one embodiment, the method further includes generating the augmented test data from previously verified test images by phase unwrapping the previously verified test image, multiplying a phase unwrapped verified test image by a constant, and phase wrapping a product test image within a range of $-\pi$ to $+\pi$ to generate a new wrap test image.

In one embodiment, the method applies randomly chosen serial image operations to the new wrap test image to develop additional test images for training the CNN.

In one embodiment, the serial image operations include at least one of deformations, rotations, and noise addition.

In one embodiment, the frames of MRI data may be image frames having displacement encoded data generated by applying multiple cycles of phase wrapping operations.

In one aspect, the present disclosure relates to a system which, in one embodiment, includes a data acquisition device configured to acquire displacement encoded magnetic resonance image (MRI) data corresponding to a cardiac region of interest of a subject. The system also includes a computer-implemented convolutional neural network (CNN), and one or more processors coupled to the data acquisition device and the CNN. The processor(s) are configured to cause the system to perform functions that include generating a phase image for each frame of the displacement encoded MRI data, wherein the phase image includes potentially phase-wrapped measured phase values corresponding to pixels of the frame; training a convolutional neural network (CNN) to compute a wrapping label map for the phase image, wherein the wrapping label map incorporates a respective number of phase wrap cycles present at each pixel in the phase image; and computing, by the trained CNN, the wrapping label map. Computing an unwrapped phase image includes adding a respective phase correction to each of the potentially-wrapped measured phase values of the phase image, wherein the phase correction is based on the number of phase wrap cycles present at each pixel. The system computes myocardial strain using the unwrapped phase image for strain analysis of the subject.

In one aspect, the present disclosure relates to a non-transitory computer-readable medium storing instructions which, when executed by one or more processors, cause one or more computing devices to perform functions for strain analysis of a cardiac region of interest of a subject from displacement encoded magnetic resonance image (MRI) data. In one embodiment, the performed functions include acquiring displacement encoded MRI data corresponding to the cardiac region of interest of the subject; generating a phase image for each frame of the displacement encoded MRI data, wherein the phase image includes potentially phase-wrapped measured phase values corresponding to pixels of the frame; and training a convolutional neural network (CNN) to compute a wrapping label map for the phase image, wherein the wrapping label map includes a respective number of phase wrap cycles present at each pixel in the phase image. The instructions are further configured for computing, by the trained CNN, the wrapping label map and computing an unwrapped phase image by adding a respective phase correction to each of the potentially-wrapped measured phase values of the phase image, wherein the phase correction is based on the number of phase wrap cycles present at each pixel. The product allows for computing myocardial strain using the unwrapped phase image for strain analysis of the subject.

Other aspects and features according to the example embodiments of the present disclosure will become apparent to those of ordinary skill in the art, upon reviewing the following detailed description in conjunction with the accompanying figures.

BRIEF DESCRIPTION OF THE DRAWINGS

Reference will now be made to the accompanying drawings, which are not necessarily drawn to scale.

FIG. 1A is a flowchart illustrating a method for performing fully-automated strain analysis for cine displacement encoding with stimulated echoes (DENSE) according to one embodiment of the present disclosure. FIG. 1B illustrates a method for performing phase unwrapping, according to one embodiment of the present disclosure.

FIG. 3 is a table showing an exemplary relationship between the phase unwrapping label definition and the corresponding class.

FIGS. 4A-4C show an example of the unwrapping problem as a first semantic segmentation problem with a single cycle of phase wrapping. FIG. 4A shows the myocardial DENSE phase image with wrapping that is the input image of the network. FIG. 4B shows the network output with the pixel-wise labels which may be classified no wrapping (red), +2π wrapping (blue), and −2π wrapping (green). The unwrapped image shown in FIG. 4C is computed from FIG. 4A by unwrapping by −π (blue) or +π (green) the classified pixels in FIG. 4B.

FIGS. 7A-7C illustrates a non-limiting example of a phase unwrapping problem as a semantic segmentation problem. FIG. 7A illustrates a myocardial DENSE phase image with wrapping is the input image of the network. FIG. 7B shows the network output of pixel-wise labels which may be classified no wrapping (red), +2π wrapping (blue), −2π wrapping (green), +4π wrapping (purple), −4π wrapping (yellow). FIG. 7C illustrates the unwrapped image computed from the images shown in in FIG. 7A by unwrapping the classified pixels shown in FIG. 7B). The top image in FIG. 7A-7C illustrates the situation in which there is one cycle of wrapping, the bottom image illustrates the situation in which there is two cycles of wrapping.

FIG. 8A shows how a new phase-wrapping pattern can be generated during data augmentation using an original wrapped image as input, performing phase unwrapping, scaling of the unwrapped phase, and wrapping to the range of (−2π, 2π). FIG. 8B demonstrates an example of serial operations to generate augmented data.

FIG. 9 is a table showing a comparison of a semantic-segmentation U-Net and the path-following method for phase-unwrapping of DENSE images of the heart. MSE values are reported for DENSE images with typical SNR and low-SNR. An asterisk indicates p<0.05.

FIG. 10A represents information from a healthy volunteer and FIG. 10B represents data from a heart failure patient.

FIG. 11A illustrates the global strains, and segmental (11B-11D) illustrates circumferential strains at end systole of basal (FIG. 11B), mid-ventricular (FIG. 11C), and apical slices (FIG. 11D) computed using the conventional user-assisted and the fully-automated DL methods.

FIG. 12 illustrates the mean and variance of mid-ventricular segmental circumferential strain obtained using the conventional user-assisted and DL-based fully-automatic methods according to one example embodiment described herein. The segments corresponded to the following data— segment 1: anteroseptal, segment 2: inferoseptal, segment 3: inferior, segment 4: inferolateral, segment 5: anterolateral, segment 6: anterior.

DETAILED DESCRIPTION

Figure 1A:
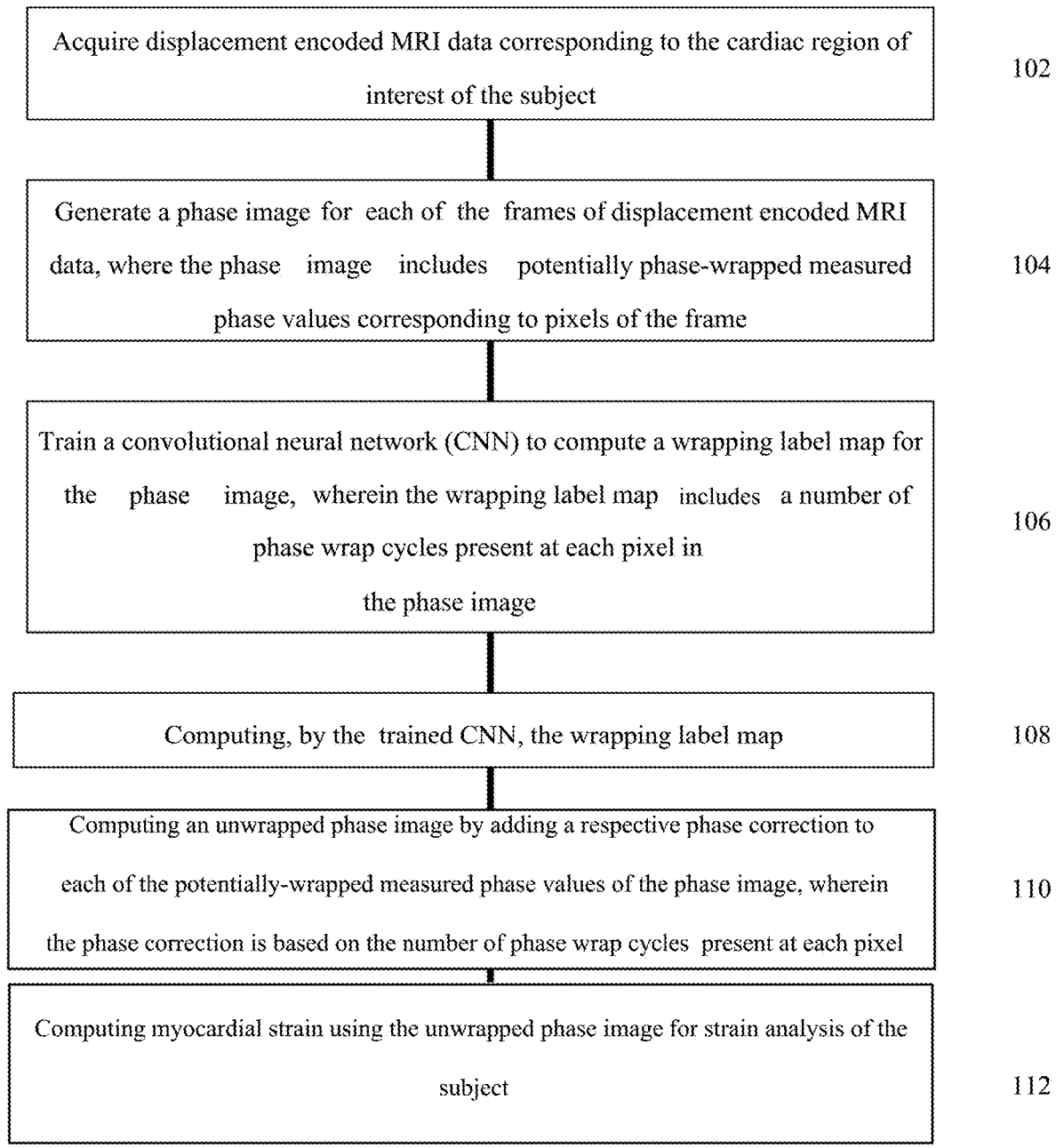
FIGS. 1A-1B are flowcharts illustrating embodiments of the present disclosure.

In some aspects, the present disclosure relates to systems, methods, and computer-readable medium for phase unwrapping for displacement encoding with stimulated echoes (DENSE) MRI using deep learning. Although example embodiments of the disclosed technology are explained in detail herein, it is to be understood that other embodiments are contemplated. Accordingly, it is not intended that the disclosed technology be limited in its scope to the details of construction and arrangement of components set forth in the following description or illustrated in the drawings. The disclosed technology is capable of other embodiments and of being practiced or carried out in various ways.

It must also be noted that, as used in the specification and the appended claims, the singular forms "a," "an" and "the" include plural referents unless the context clearly dictates otherwise. Ranges may be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

In describing example embodiments, terminology will be resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method may be performed in a different order than those described herein without departing from the scope of the disclosed technology. Similarly, it is also to be understood that the mention of one or more components in a device or system does not preclude the presence of additional components or intervening components between those components expressly identified.

Some references, which may include various patents, patent applications, and publications, are cited in a reference list and discussed in the disclosure provided herein. The citation and/or discussion of such references is provided merely to clarify the description of the disclosed technology and is not an admission that any such reference is "prior art" to any aspects of the disclosed technology described herein. All references cited and discussed in this specification are incorporated herein by reference in their entireties and to the same extent as if each reference was individually incorporated by reference.

As discussed herein, a "subject" (or "patient") may be any applicable human, animal, or other organism, living or dead, or other biological or molecular structure or chemical environment, and may relate to particular components of the subject, for instance specific organs, tissues, or fluids of a subject, may be in a particular location of the subject, referred to herein as an "area of interest" or a "region of interest."

Throughout the description, the following abbreviations may be used:
DENSE—Displacement Encoding with Stimulated Echoes;
MRI—Magnetic Resonance Imaging;
CNN—Convolutional Neural Network;
LV—Left Ventricular;
RV—Right Ventricular;
HF—Heart Failure;
EF—Ejection Fraction;
DL—Deep Learning;
MSD—Mean Surface Distance;
MSE—Mean Squared Error;
SNR—Signal to Noise Ratio;
NW—No Wrap; and
Ecc—Circumferential Strain.

A detailed description of aspects of the present disclosure, in accordance with various example embodiments, will now be provided with reference to the accompanying drawings. The drawings form a part hereof and show, by way of illustration, specific embodiments and examples. In referring to the drawings, like numerals represent like elements throughout the several figures.

Embodiments of the present disclosure include DL-based fully-automated methods for global and segmental strain analysis of short-axis DENSE MRI from a multicenter dataset. U-Nets were designed, trained and found to be effective for LV segmentation, identification of the anterior RV-LV insertion point, and phase unwrapping. Steps involving displacement and strain calculations can be automated, thus, with the DL methods, the entire DENSE analysis pipeline for global and segmental strain can be fully automated. Identification of the anterior RV insertion point, and phase unwrapping, and remaining steps to compute displacement and strain can also be performed automatically without user assistance, as described herein[4,5,17,18].

Embodiments of the present disclosure include a fully-automated post-processing approach for cine displacement encoding with stimulated echoes (DENSE). Deep learning (DL) methods, particularly convolutional neural networks (CNN), can be used segmentation and analysis of various CMR techniques[19,20,29,21-28]. Some embodiments of the present disclosure include a pipeline for fully-automated analysis of cine DENSE data using four CNNs to (a) identify the LV epicardial border, (b) identify the LV endocardial border, (c) identify the anterior RV-LV insertion point, and (d) after LV segmentation, perform phase unwrapping of the LV myocardium. Embodiments of the present disclosure include a pipeline that can eliminate all user intervention and can reduce the time for image analysis.

Embodiments of the present disclosure include a fully-automatic DENSE analysis pipeline. Some embodiments of the present disclosure include the following general steps: (a) LV segmentation, (b) identification of the anterior RV-LV insertion point, (c) phase unwrapping, and (d) displacement and strain analysis. Steps (a)-(c) can utilize CNNs, and step (d) can use other fully-automatic methods[5,31].

Figure 1B:
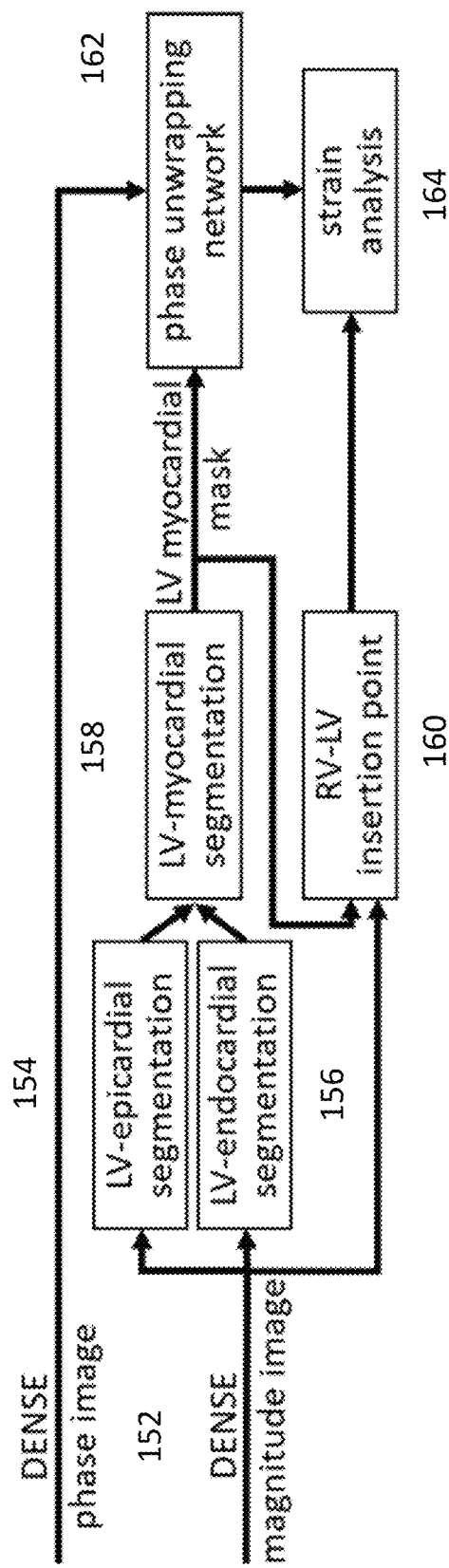

FIGS. 1A-1B illustrate flowcharts of methods for performing segmentation and phase unwrapping according to embodiments of the present disclosure.

With reference to FIG. 1A, a flowchart illustrating a method for performing phase unwrapping is illustrated. At step 102, MRI data is acquired that corresponds to a region of interest of the subject (e.g. a cardiac region). For embodiments herein, the MRI data is stored in computerized memory and may be manipulated to achieve the goals of this disclosure. For example, the data can be subject to computerized mathematical processes in which various forms digital data are created from the original MRI data. In the examples herein, the MRI data may be referred to in terms of frames of image data, and the image data may be stored in appropriate software and hardware memory structures, including but not limited to image arrays configured to allow calculations and mathematical manipulation of the original image data.

In some embodiments, the MRI images may be subject to segmentation operations, including but not limited to those set forth in U.S. patent application Ser. No. 16/295,939 filed on Mar. 7, 2019, and published as United States Pub. No. 2019/0279361, which is incorporated by reference herein. This disclosure utilizes segmented images of the epicardial contour and endocardial contour, such as the segmented images illustrated in FIG. 2, although the use of other types and configurations of images is contemplated.

At step 104, a phase image, which may be stored in a computer as a phase image or phase image array or matrix, is generated for each frame, including a phase value corresponding to the pixels of each frame. The method can include generating a phase image for each frame of the displacement encoded MRI data. A chart showing a non-limiting example of the labels used for different types of wrapping is shown in FIG. 3, and the labels shown in FIG. 3 may be referred to throughout the present disclosure. The phase image can include potentially-phase-wrapped measured phase values corresponding to pixels of the frame.

At step 106, a convolutional neural network (CNN) is trained to compute a wrapping label map for the phase image, where the wrapping label map includes a number of phase wrap cycles present at each pixel in the phase image. The wrapping label map can, for example use the labels shown in FIG. 3 or any other suitable labels.

Figures 4A, 4B, 4C:
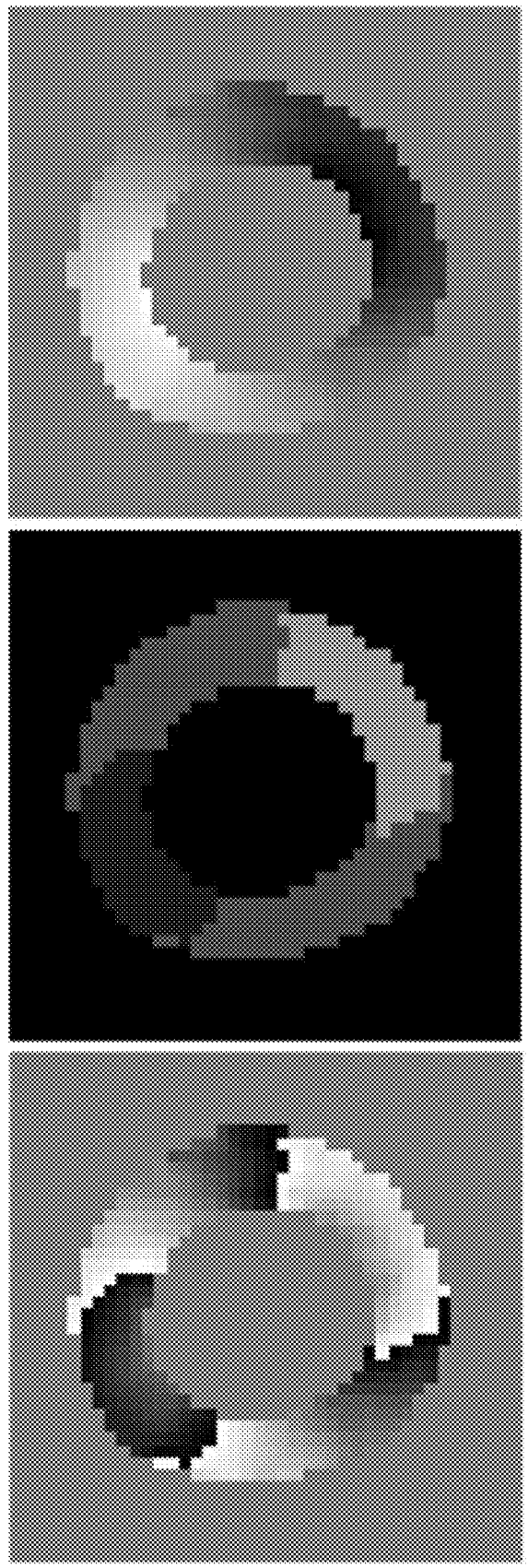
FIGS. 4A-4C are demonstrations of phase unwrapping using a semantic-segmentation U-Net.

At step 108, the CNN is used to compute a wrapping label map as shown in FIGS. 4A-4B. An example input image including phase wrapping is shown in FIG. 4A. The wrapping label map (FIG. 4B) includes regions classified by the CNN as corresponding to +2pi and −2pi wrapping.

An unwrapping factor can be calculated for each region classified by the CNN, based on the classification of each region. As a non-limiting example, in some embodiments of the present disclosure, every "cycle" of wrapping corresponds to the phase being $2\pi$ off from the "true" phase value. Therefore, based on the classification of each pixel as being wrapped or not, and in which direction the phase is wrapped (i.e. in the positive or negative direction), the appropriate unwrapping factor can be calculated for each pixel.

At step 110, therefore, the method includes computing an unwrapped phase image by adding a respective phase correction to each of the potentially-wrapped measured phase values of the phase image, wherein the phase correction is based on the number of phase wrap cycles present at each pixel.

In phase-reconstructed MR images, the phase value is inherently confined to the range $(-2\pi, 2\pi)$. However, in cardiac DENSE in order to balance displacement sensitivity, signal-to-noise ratio, and suppression of artifact-generating signals, displacement-encoding frequencies that lead to phase shifts of greater than $2\pi$ are typically used, and $\pm 1$ cycle of phase wrapping typically occurs during systole[5]. Thus, phase unwrapping can be required to convert phase to displacement.

The unwrapped phase $\psi_{ij}$ can be estimated from the potentially-wrapped measured phase $\varphi_{ij}$ as follows:

$$\psi_{ij} = \varphi_{ij} + 2\pi k_{ij}$$

where $k_{ij}$ is an integer and where $-2\pi < \varphi_{ij} < 2\pi$. According to some embodiments of the present disclosure phase unwrapping problem requires determining $k_{ij}$ for each pixel indexed by i and j. Thus, the phase unwrapping can be defined as a semantic segmentation problem[35], and the network can label each pixel as belonging to one of at least three classes (no wrap, $-2\pi$ wrapped, or $+2\pi$ wrapped) as shown in FIG. 3.

At step 112, and with the unwrapping complete, the method of this disclosure may be used to compute myocardial strain using the unwrapped phase image for strain analysis of the subject.

To create the ground truth for unwrapped phase images, a highly accurate but very slow phase unwrapping method based on multiple phase prediction pathways and region growing can be used[36]. Additionally, a user can also check the results of this method, frame by frame, and discard all frames with unwrapping errors. The same dilated U-Net structure with three output classes was trained using a pixel-wise cross-entropy loss function. The network's input was the segmented phase-reconstructed DENSE image and the output was the wrapping label map. With this design, after applying the CNN, the value of $k_{ij}$ is known for each pixel. Then by multiplying $k_{ij}$ by $2\pi$ and adding the result to the input wrapped image, the unwrapped phase is computed.

Based on whether there is $+2\pi$ wrapping or $-2\pi$ wrapping, the appropriate $+2\pi$ or $-2\pi$ phase correction can be added to the image to com, to compute 110 an accurate output image, as shown in FIG. 4C.

Figure 5:
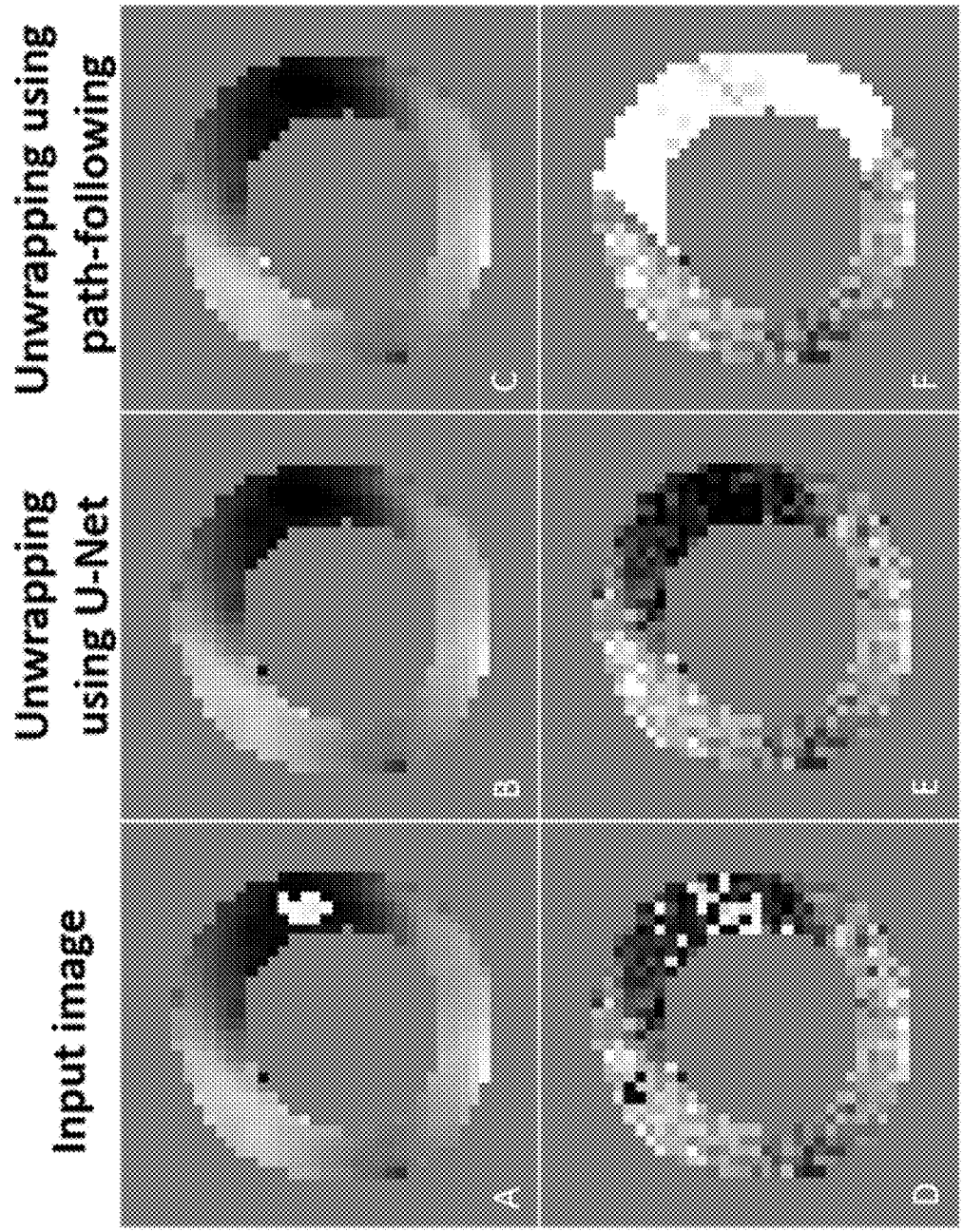
FIG. 5 illustrates results of an improved phase unwrapping of low-SNR data using the U-Net. The top row shows an example with high SNR where the U-Net and the path-following method are both successful (A-C). When noise was added to (A) to create low-SNR data (D), the U-Net successfully unwrapped the low-SNR image (E) whereas the path-following method failed (F).

The CNN can be used to generate a more accurate wrapping label map than path-following approaches. As shown in FIG. 5, the top row illustrates low-noise images, and the bottom row illustrates high-noise images. The CNN correctly identified wrapping in the high noise areas, while the path following technique failed and did not correctly perform phase unwrapping on the high-noise image.

Figure 6:
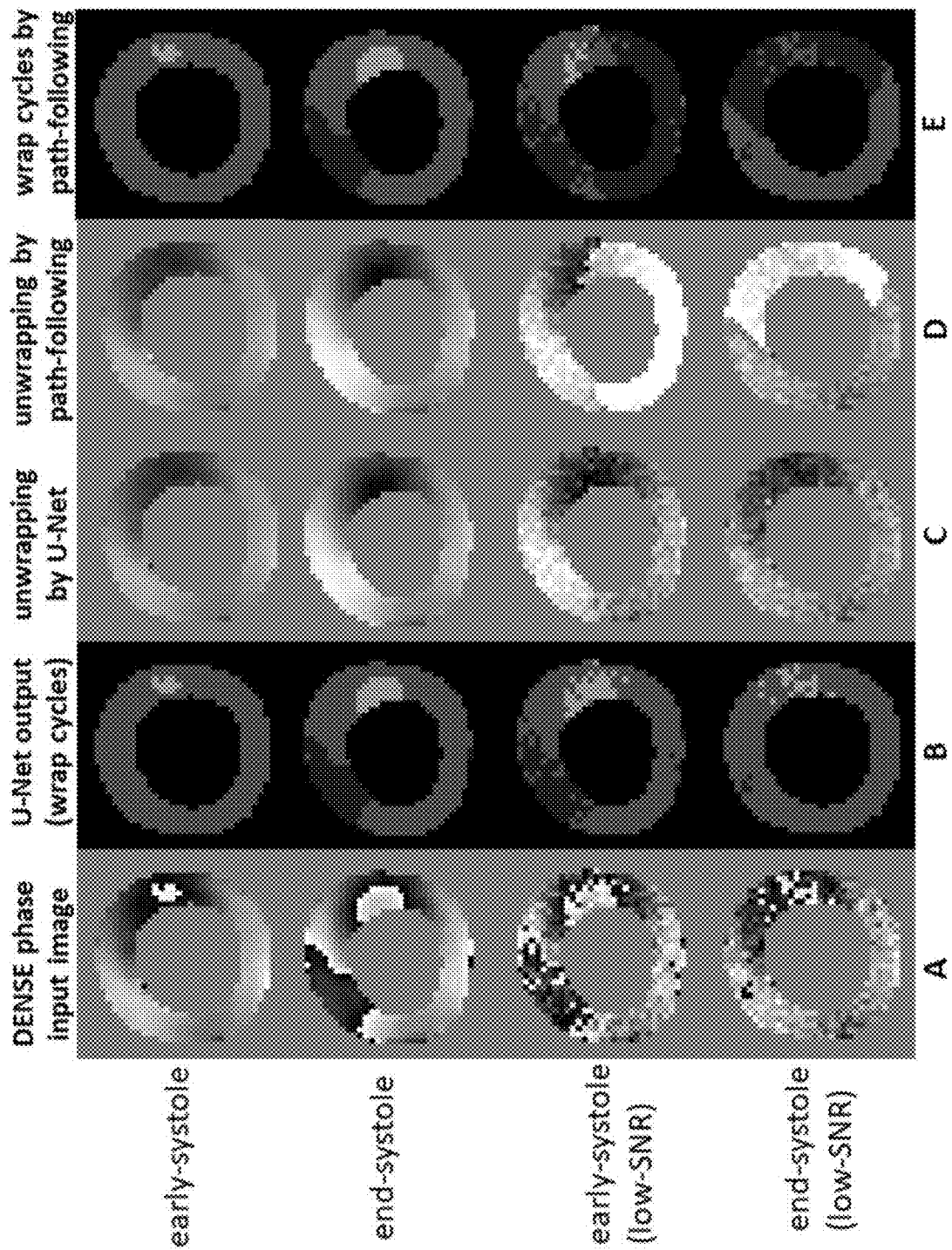
FIG. 6 shows a comparison of phase unwrapping using a semantic-segmentation U-Net as compared with the path-following method. For DENSE images with typical SNR (top two rows), the semantic segmentation U-Net correctly identified wrapped pixels (second column). Both the U-Net and the path-following methods performed phase unwrapping without errors (top two rows, columns C-D). For low-SNR data (bottom two rows), the U-Net successfully performed semantic segmentation and phase unwrapping, however the path-following method led to large phase-unwrapping errors, which are also depicted in wrap cycle maps (E).

Similarly, FIG. 6 illustrates a variety of phase unwrapping scenarios, showing the advantage of the U-Net and CNN based approach over path-following approaches.

Additionally, embodiments of the present disclosure can perform phase unwrapping for images with more than one "cycle" of phase wrapping. For example, with reference to FIGS. 7A-7C, a myocardial DENSE phase image is shown in the bottom row that includes regions with both 1 and 2 cycles of phase wrapping. The network output is the pixel-wise labels which may be classified no wrapping (red), $+2\pi$ wrapping (blue), $-2\pi$ wrapping (green), $+4\pi$ wrapping (purple), $-4\pi$ wrapping (yellow) (FIG. 7B). The unwrapped image (FIG. 7C) is computed from (FIG. 7A) by unwrapping the classified pixels in (FIG. 7B). First row shows an example of one wrap cycle, second row shows same example with two wrap cycles. It should be understood that in situations where there is additional wrapping, (e.g. two cycles of wrapping, three cycles of wrapping, four cycles of wrapping etc.) the network can be configured to classify the additional regions. For example, as shown in the non-limiting example in FIGS. 7A-7C, embodiments of the present disclosure configured to perform two cycles of phase unwrapping can include 5 classifications (no wrapping, $+2\pi$ or $-2\pi$ unwrapping, and $+4\pi$ or $-4\pi$ unwrapping).

Optionally, these 5 types of wrapping can correspond to the following classifications: 1—no wrap (k=0), 2-($-2\pi$) wrap (k=$-1$), 3—($+2\pi$) wrap (k=$+1$), 4—($-4\pi$) wrap (k=$-2$), and 5—($+4\pi$) wrap (k=$+2$). It should be understood that these classifications are intended only as non-limiting examples, and that different numbers of classifications and different systems for naming, labeling, and organizing classifications are contemplated by the present disclosure. Similarly, it should be understood that in embodiments of the present disclosure capable of performing more than two cycles of phase unwrapping, that more than 5 classifications can be used.

With reference to FIG. 1B, a flowchart illustrating a method for performing strain analysis is shown, according to one embodiment of the present disclosure.

At step 152, Phase encoded MRI data corresponding to the cardiac region of interest of the subject is acquired. The MRI data can be acquired using a Cine DENSE image acquisition protocol. Optionally, segmentation can be performed including LV-epicardial segmentation 154, LV-endocardial segmentation 156, and LV-myocardial segmentation 158.

LV Segmentation 154, 156, 158 can be performed using a convolutional neural network. Embodiments of the present disclosure implement a 2D U-Net approach to LV segmentation [e.g.[19-22,24,26,28]], LGE[27], $T_1$-weighted MRI[25] and phase contrast[23]. Three-dimensional convolutions may have advantages for segmentation of cine MRI data through time; however, they can be less well studied for cardiac cine MRI than 2D and can present unique issues (e.g. they can require a constant number of cardiac phases). For cine MRI, to date most studies use a 2D model and achieve very good results[26,28,41]. Since 2D models work well and DICE values can be reasonably good using a 2D approach, a 2D U-Net can be used. Also, values for HD and MSD can be similar to the mean contour distance of 1.14 mm and HD of 3.16-7.25 mm for myocardial segmentation reported by others[19], and to the average perpendicular distance of 1.1±0.3 mm also reported by others[26]. Embodiments of the present disclosure use two separate U-Nets for epicardial and endocardial segmentation, although in some applications training one network for myocardial segmentation based on the proposed network architecture can result in the same performance. Optionally, three classes of the blood pool can be defined, myocardium and background and to assign class weights of 3, 5 and 1, respectively, which can overcome the imbalanced classes problem.

To create the ground-truth LV segmentation data, manual image annotation can be performed for DENSE magnitude-reconstructed images. The LV endocardial and epicardial borders can be manually traced for all frames using DENSE-analysis software[17]. To automatically segment the LV from DENSE magnitude images, one U-Net was trained to extract the epicardial border, and another to extract the endocardial border, and the myocardial pixels can be identified by performing a logical XOR between the two masks. The 2D U-Net networks utilized the structure presented by Ronneberger[32] with modifications to get the best results for the proposed application. Specifically, in the contracting path, each encoding block can contain two consecutive sets of dilated convolutional layers with filter size 3×3 and dilation rate 2, a batch normalization layer and a rectified linear activation layer. Compared with traditional convolutions, dilated convolutions can increase the receptive field size without increasing the number of parameters and showed improved performance in our experiments. Padding can be used in each convolutional operation to maintain the spatial dimension. Between each encoding block, pooling layers with step size of 3×3 and stride 2 were applied to reduce the spatial dimension in all directions. The number of features can be doubled for the next encoding block.

Four symmetric encoding and decoding blocks were used in the contracting and expanding path, respectively. Each decoding block can contain two consecutive sets of deconvolutional layers with filter size 3×3, a batch normalization layer and a rectified linear activation layer. The output of each encoding block in the contracting path was concatenated with those in the corresponding decoding block in the expanding path via skip-connections. The final segmentation map can include two classes: background and endocardium or epicardium. The loss function can be the summation of the weighted pixel-wise cross entropy and soft Dice loss. The assigned class weights were 1 for background, 2 for endocardium in the endocardial network and 3 for the epicardial network. During training, data augmentation on-the-fly was performed by applying random translations, rotations and scaling followed by a b-spline-based deformation to the input images and to the corresponding ground-truth label maps at each iteration. This type of augmentation has the advantage that the model sees different data at each iteration. The use of other network configurations, including networks with different numbers of layers, different filter sizes, stride numbers and dilation rates, is contemplated by the present disclosure, and the above are intended only as non-limiting examples of network parameters that can be used for segmentation.

In one embodiment of the present disclosure, 400 epochs were used to train each network; therefore, each image was augmented 400 times. After applying the random transformations to the label maps, a threshold value of 0.5 was applied to the interpolated segmentation to convert back to binary values[33]. To improve the accuracy and smoothness of the segmented contours, during testing, each image can be rotated 9 times at an interval of 40 degrees and the corresponding output probability maps were rotated back and averaged[34]. Hereafter, this testing process is described in the present disclosure as "testing augmentation". It should be understood that the number of rotations (9), the interval (of 40 degrees), the number of epochs (400), and the threshold value (0.5) as well as this order and selection of steps for testing augmentation, are included only as non-limiting examples of ways to improve the accuracy of he described network, and that the use of other training techniques is contemplated.

Based on the segmentation 104 106 108 the RV-LV insertion point can be identified 110. The anterior RV-LV insertion point is the location of the attachment of the anterior RV wall to the LV, and its location defines the alignment of the American Heart Association 16-segment model[16] which can be used for segmental strain analysis of the LV. As the first frame of cine DENSE images can have poor blood-myocardium contrast, a U-Net is trained to detect the anterior RV-LV insertion point on early-systolic frames (e.g. frames 5 and 6), where the insertion point is reliably well visualized. To create the ground-truth data, an expert user can identify one point in these frames from magnitude-reconstructed DENSE images. During network training, instead of using that point as an absolute ground-truth, which only provides very limited information to the network to learn and suffers from severe class imbalance, a circle with a six-pixel radius around that point can be defined as the network target. The network's inputs were the DENSE magnitude image and the segmented LV binary mask obtained by the aforementioned myocardial segmentation networks as an additional input channel. The network's output is the probability map of a circle for which the center of mass is defined to be the detected RV-LV insertion point. The same aforementioned U-Net structure can be used. The loss function was the combination of the absolute difference and the soft Dice between the target and the output probability map computed using a Sigmoid function. The same on-the-fly data augmentation can be applied during training, and optionally testing augmentation may not be used in the network.

At step 162, phase unwrapping can be performed, for example according to the method illustrated in FIG. 1A, or other methods described herein.

At step 164, the unwrapped phase image can be used to perform strain analysis, based on the relationship between the phases in the unwrapped phase image and displacement. This can include determining correlation of the unwrapped phase image to strain values for strain analysis of the subject.

Figure 8A:
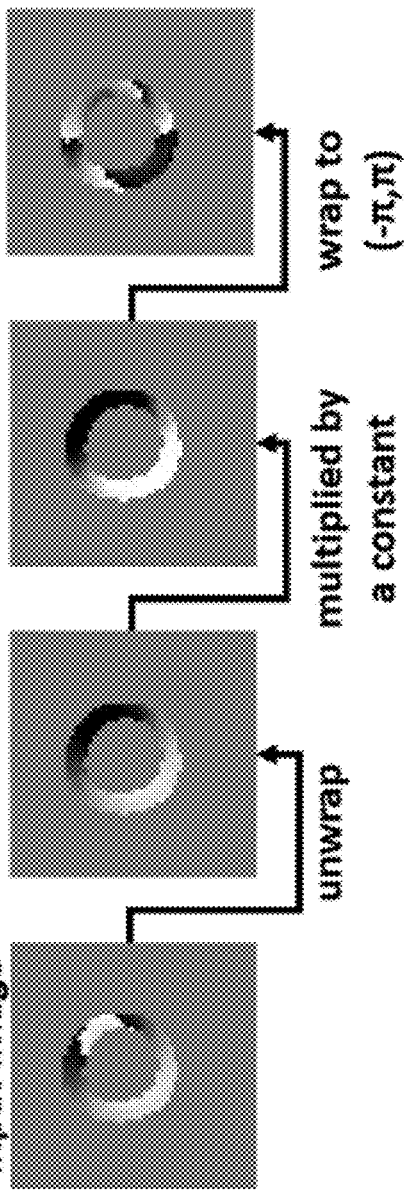
FIGS. 8A-8B illustrate a method for performing data augmentation for the phase-unwrapping CNN.
Figure 8B:
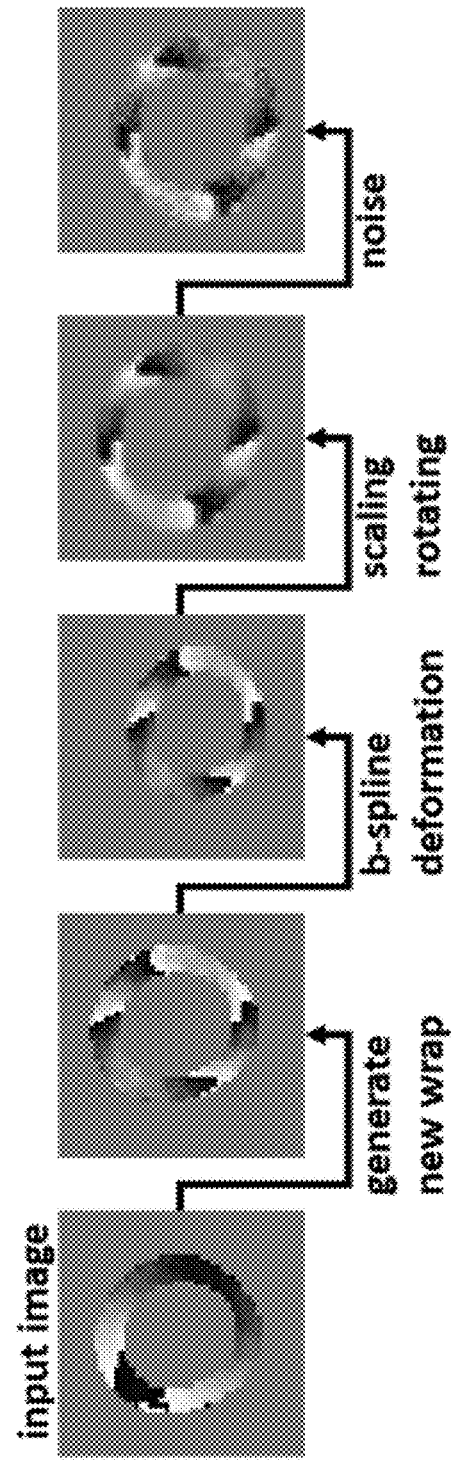

Optionally, the method can include testing and/or training augmentation. As shown in FIGS. 8A-8B, transformations can be applied to generate training images with different qualities. Training augmentation can also be performed by adding Gaussian noise with a mean of zero and a randomly chosen standard deviation between (e.g. 0, 0.75) to simulate different signal-to-noise ratios and by manipulating the unwrapped ground truth data to generate new wrapped data. Data augmentation can be an important point as it can avoid overfitting and the network is trained on data with lower SNR and more wrapping patterns. To create augmented new wrapped data, an unwrapped ground-truth phase image can be multiplied by a random constant number (e.g. between 0.8 and 2.0), and then it is wrapped to the range $(-2\pi, 2\pi)$. For each augmented phase image, the $k_{ij}$ value is known and if it is 0, 1, or −1 then it is used for training. FIG. 8A illustrates how a new phase-wrapping pattern is generated during augmentation and FIG. 8B demonstrates an example of how different operations can be applied to create augmented data. For this network, the randomly generated transformations including combinations of translation, rotation, scaling, shearing, and b-spline deformation and applied them to the training images along with random phase manipulation and random noise. Different augmentation/transformations can be applied to each image, as a non-limiting example, in FIGS. 8A-8B, 7 random augmentations were applied to each training image. Again, it should be understood that the standard deviations and constants used to perform training augmentation are intended only as non-limiting examples, and other types of training augmentation are contemplated by the present disclosure.

For data augmentation, segmented and phase unwrapped data obtained by applying segmentation and phase unwrapping methods, can be used. Using simple manipulations of these data, as shown in FIGS. 8A-B, augmented pairs of wrapped and unwrapped images can be generated with new wrapping patterns, providing an effective data augmentation strategy for training the phase-unwrapping U-Net. This strategy can be used to create a robust and successful CNN. The phase-unwrapping problem can potentially be treated different approaches. One approach is to train a network to directly estimate the unwrapped phase from the potentially-wrapped input phase, i.e., treating the problem as a regression problem[42,43]. Another approach, used in some embodiments of the present disclosure, is to estimate the integer number of wrap cycles at each pixel of the phase map by training a semantic-segmentation network to label each pixel according to its wrap class as defined in FIG. 3[35,44-46]. The semantic-segmentation approach can recognize DENSE phase wrap patterns, and embodiments of the present disclosure using the semantic segmentation approach can be effective even for low-SNR images.

Example Implementations and Corresponding Results

The following description includes discussion of example implementations of certain aspects of the present disclosure described above, and corresponding results. Some experimental data are presented herein for purposes of illustration and should not be construed as limiting the scope of the disclosed technology in any way or excluding any alternative or additional embodiments.

An embodiment of the present disclosure including a semantic-segmentation phase-unwrapping network was compared to path-following for low-SNR data. To validate one embodiment of the present disclosure, each new step was be compared with expert-user or ground-truth methods and the end-to-end processing of global and segmental strains were compared to previously-validated user-assisted conventional DENSE analysis methods[17].

An embodiment of the present disclosure was tested using Cine DENSE image acquisition parameters including a pixel size of 1.56×1.56 mm²-2.8×2.8 mm², FOV=200 mm² (using outer volume suppression) to 360 mm², slice thickness=8 mm, a temporal resolution of 17 msec (with view sharing), 2D in-plane displacement encoding using the simple three-point method[30], displacement-encoding frequency=0.1 cycles/mm, ramped flip angle with final flip angle of 15°, echo time=1.26-1.9 msec, and a spiral k-space trajectory with 4-6 interleaves.

Short-axis cine DENSE MRI data from 38 heart-disease patients and 70 healthy volunteers were used for network training and testing of a non-limiting example of the present disclosure. Twenty-six datasets were acquired using 1.5T systems (Magnetom Avanto or Aera, Siemens, Erlangen, Germany) and 82 were acquired using 3T systems (Magnetom Prisma, Skyra, or Trio, Siemens, Erlangen, Germany). The types of heart disease included dilated cardiomyopathy, hypertrophic cardiomyopathy, coronary heart disease, hypertension, acute coronary syndrome and heart failure with left bundle branch block. For each subject, 1-5 short-axis slices were acquired, each with 20-59 cardiac phases. Training data included 12,415 short-axis DENSE images from 64 randomly selected subjects, and 20% of all training data were used for model validation. Forty-four datasets, including 25 healthy volunteers and 19 patients imaged at both field strengths, were selected for the test data (10,510 total 2D images, including those with displacement encoded in both the x- and y-directions).

In the experimental embodiment described herein, the final model of each network was trained using data from 64 subjects. Network training was performed on an Nvidia Titan Xp GPU with 12 GB RAM over 400 epochs using an Adam optimizer at a learning rate of 5E-4 and a mini batch size of 10. The times to train the myocardial segmentation networks (endocardium and epicardium), identifying the RV-LV insertion point network, and using the myocardial segmentation for the phase unwrapping network were 34, 48, and 30 hours, respectively. The networks were implemented using Python (version 3.5; Python Software Foundation, www.python.org) with the Tensorflow machine-learning framework (version 1.12.0)[37].

To quantitatively evaluate the results of myocardial segmentation, the DICE similarity coefficient[38] was computed. This metric measures the overlap between the ground-truth segmentation (A) and the CNN's segmentation (B) as follow:

$$DICE = \frac{2 \times |A \cap B|}{|A| + |B|} \quad (2)$$

DICE coefficient is normalized between 0 and 1, where "0" indicates complete dissimilarity and "1" indicates complete agreement.

In addition, to measure the maximum and average distances between the myocardial ground-truth and the CNN-generated contours, the Hausdorff distance ($D_H$) and the mean surface distance (MDS) were computed as follows. Given two sets of points A=($a_1$, ..., $a_n$) and B=($b_1$, ..., $b_m$), and an underlying distance d(a, b) which is defined as the Euclidean distance d (a, b)=∥a−b∥, $D_H$ and MDS are given by:

$$D_H(A, B) = \max(h(A, B), h(B, A)) \quad (3)$$

$$h(A, B) = \max_{a \in A}(\min_{b \in B} d(a, b))$$

$$MSD = \mathrm{mean}(h_{mean}(A, B), h_{mean}(B, A)) \quad (4)$$

$$h_{mean}(A, B) = \frac{1}{n}\sum_{a \in A}(\min_{b \in B} d(a, b))$$

To assess the accuracy of identifying the RV-LV insertion point position, the Euclidean distance between the expert-selected point and the centroid of the automatically-selected region was calculated.

To evaluate the phase-unwrapping CNN, it was compared with the widely-used path-following method[5] using mean squared error (MSE). The ground-truth unwrapped phase was computed using the phase-unwrapping method based on multiple phase prediction pathways and region growing[36].

For images with SNR typical of routine DENSE protocols[15,39] (phase SNR of approximately 22), MSE referenced to ground truth were evaluated for the proposed U-Net and the path-following method. Similar to the phase SNR of velocity-encoded phase contrast imaging[40], the DENSE phase SNR was calculated as $$\text{phase } SNR = \left\|\frac{\text{mean(unwrapped phase of end} - \text{systolic } ROI)}{stdev(\text{phase of end} - \text{diastolic myocardium})}\right\|$$

where the mean unwrapped phase of an end-systolic region of interest (ROI) measures the DENSE phase in the region with greatest displacement (representing the signal of interest), and the standard deviation of the phase of the end-diastolic myocardium provides a measure of the standard deviation of phase at a cardiac frame where the mean phase is essentially zero. Because SNR can be lower than typical in some circumstances (such as when imaging patients with implanted devices), the two methods were also analyzed for lower SNR data generated by adding noise to our datasets. For low-SNR data, if no ground truth data is available, low-SNR data (with phase SNR=5-10) can be synthetically created from the test data by adding noise with zero mean and with standard deviation of 0.75. Adding noise to the original wrapped phase data could change the wrapping class of any image pixel. As the label of the pixel may not be the same as the corresponding pixel in the original data, for the low-SNR data the U-Net was compared with the path-following method by calculating the MSE between the unwrapped phase and the typical-SNR unwrapped ground truth.

Figure 1C:
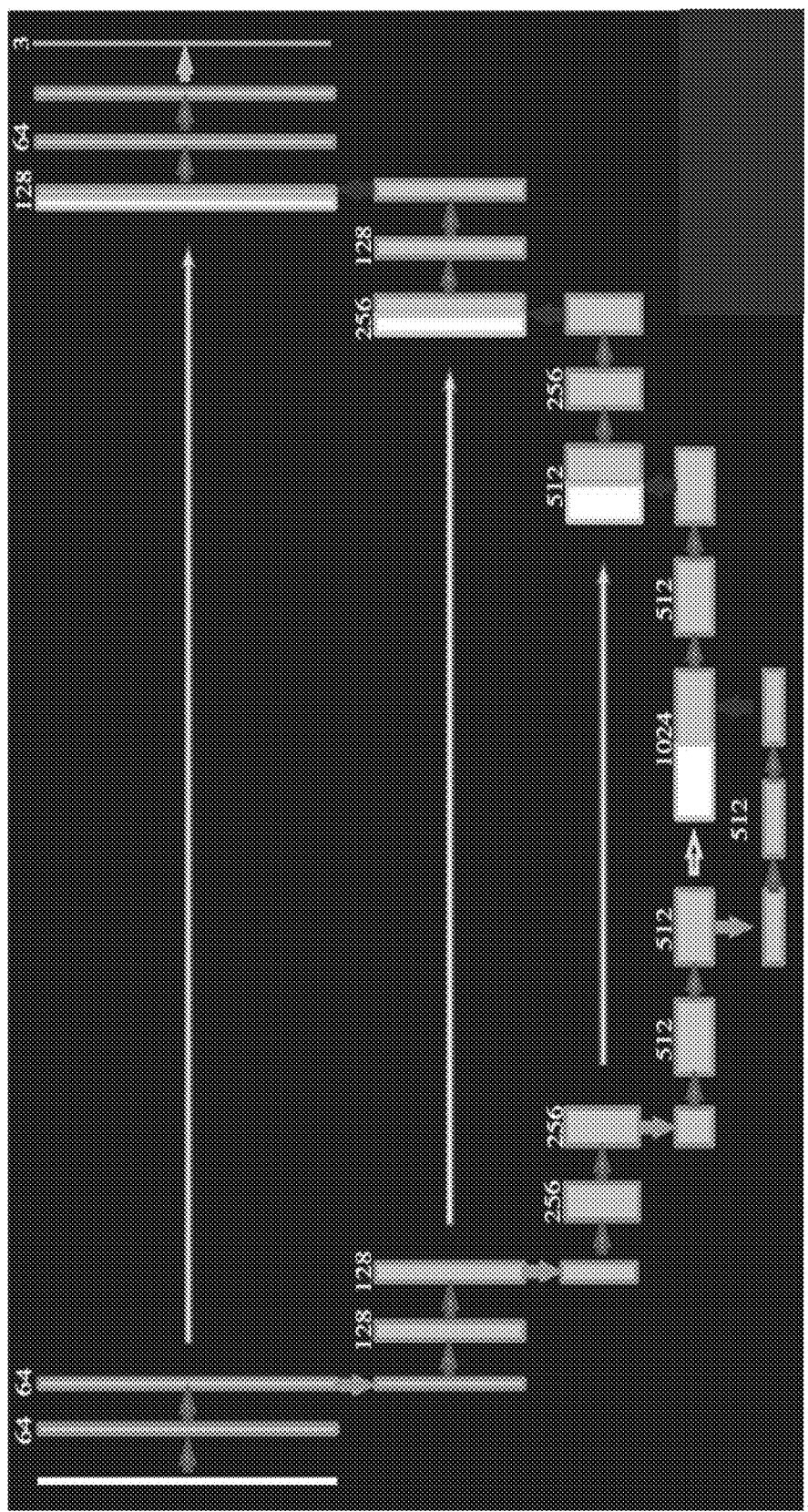
FIG. 1C is a schematic diagram of an example convolutional neural network (CNN) according to embodiments of the present disclosure. The CNN is a U-Net that used dilated convolutions of rate 2 in the contracting path, a pixel-wise cross-entropy loss function, Adam optimizer (learning rate of 5E-4, a mini batch size of 10), dropout rate of 0.5, and epochs of 200. Brown/Gold arrows represent convolutions of 3×3+batch normalization+ReLU; the blue arrows represent pooling of 3×3 with a stride of 2, the red arrows represent deconvolutions of 2×2, the purple/pink arrows from one side of the U-Net to the other are concatenations, and the final light orange arrow represents convolutions of 1×1+Softmax for the right side output.

To evaluate the full pipeline shown in FIG. 1 for global and segmental circumferential strain analysis of the LV, correlations and Bland-Altman analyses were performed comparing the proposed deep-learning based method and the conventional user-assisted semi-automated method (DENSEAnalysis,[17]). In DENSEAnalysis, a $10^{th}$-order polynomial was used for temporal fitting and a spatial smoothing parameter of 0.8 was selected.

This example focused on results for circumferential strain and not for radial strain. There are fewer pixels radially across the LV wall in short-axis images than circumferentially. For this reason, methods like DENSE and tagging can be less accurate and reproducible for the estimation of radial strain compared to circumferential strain, and many clinical applications of short-axis DENSE (and tagging) find that circumferential strain is diagnostically or prognostically useful, whereas radial strain may not perform as well.

In this non-limiting example implementation, all cardiac phases were segmented, with good results, although it is also contemplated that manually drawn-contours could be used for segmentation. Further, the DL methods described herein provide a superset of the contours needed for the simplified method, and a DL-based simplified method is contemplated.

While other strain imaging methods may provide reliable and reproducible global strain, values and are well-suited to automatic DL-based analysis[20,28,29], cine DENSE has shown excellent reproducibility of segmental strain[7]. The example described herein shows excellent agreement of DL-based fully-automated segmental strain with user-assisted semi-automatically computed segmental strain. The limits of agreement for DL automatic vs. user-assisted segmental circumferential strain are better than those for DL vs. user-assisted analysis of myocardial-tagging-based global circumferential strain[29]. A potential explanation for the substantially better results for DENSE is that for tag analysis, DL is used to perform motion tracking, and even when trained using data from thousands of subjects, there is error in motion tracking[29]. In contrast, for DENSE, DL is used only for segmentation and phase unwrapping, but DL is not used for automatic motion estimation. For DENSE, during data acquisition displacement is encoded directly into the pixel phase, thus there is no need to learn motion estimation from image features. In essence, the motion estimation problem for DENSE is much simpler than for methods like tagging and feature tracking, and the demands for DL to accomplish full automation are much less.

Figure 2:
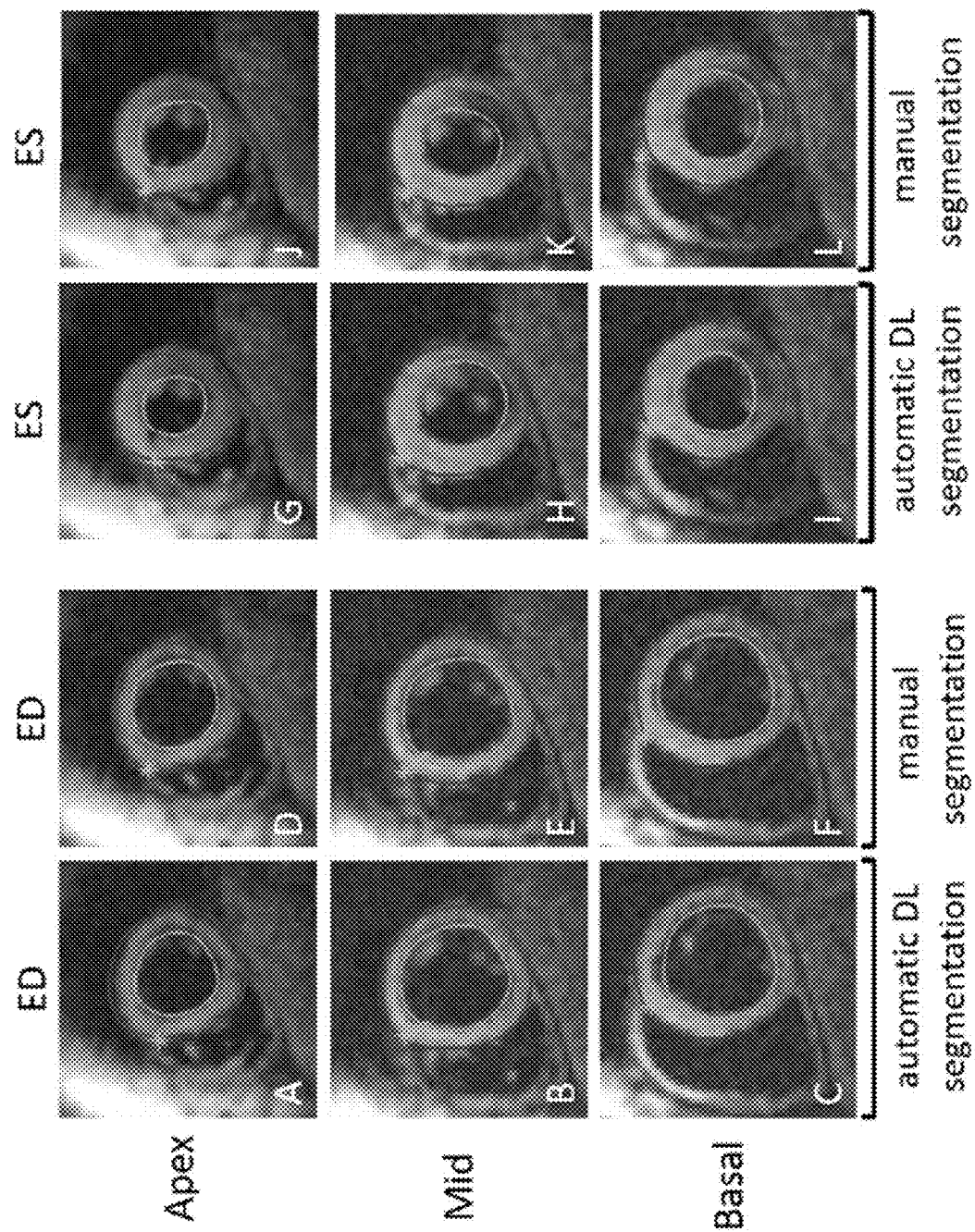
FIG. 2 illustrates an example of automatic DL LV segmentation and identification of anterior RVLV insertion points by U-Nets (boxes A-C, G-I), and the corresponding results provided by an expert user (boxes D-F, J-L). Results are shown at end diastole (ED) and end systole (ES). The epicardial contour is the outer circle, the endocardial contour is the inner circle, and the anterior RV-LV insertion point is depicted with an asterisk.

Evaluation of the U-Nets for LV segmentation using 5,255 test images resulted in a DICE coefficient of 0.87±0.04, a Hausdorff distance of 2.7±1 pixel (equivalent to 5.94±2.2 mm), and a mean surface distance of 0.41±0.29 pixels (0.9±0.6 mm). The computation times for determining the epicardial and endocardial contours for a single DENSE image, including test augmentation, were 0.16±0.02 s, 0.15±0.01 s, respectively. The typical semi-automatic LV segmentation time for DENSE is 3-5 minutes for all cardiac phases, which corresponds to about 6 s per frame. The RV-LV insertion point was detected within 1.38±0.9 pixels compared to the manually annotated data. The computation time for detecting the RV-LV insertion point was 2.4±0.15 s for all cardiac phases. An expert reader uses approximately 20 seconds to manually define the point. FIG. 2 shows examples of the automatically and manually segmented LV epicardial and endocardial contours and the identification of the anterior RV-LV insertion point on short axis images at end-diastolic (ED) and end-systolic (ES) frames.

The phase-unwrapping U-Net performed well on both typical-SNR and low-SNR DENSE phase images. The MSE values for the semantic-segmentation U-Net and the standard path-following method are provided in Table 2. MSE was similar for typical-SNR data using the U-Net and conventional path following, and was lower for low-SNR data using the U-Net (p<0.05). The time for DL phase unwrapping for all cardiac phases was 3.52±0.21 s, which was similar to path following method of 3.50±0.65 s. FIG. 6 4 illustrates an example where the U-Net and the path-following method were both successful for typical-SNR data and where the semantic-segmentation U-Net outperformed the path-following method for low-SNR data.

Figure 10A:
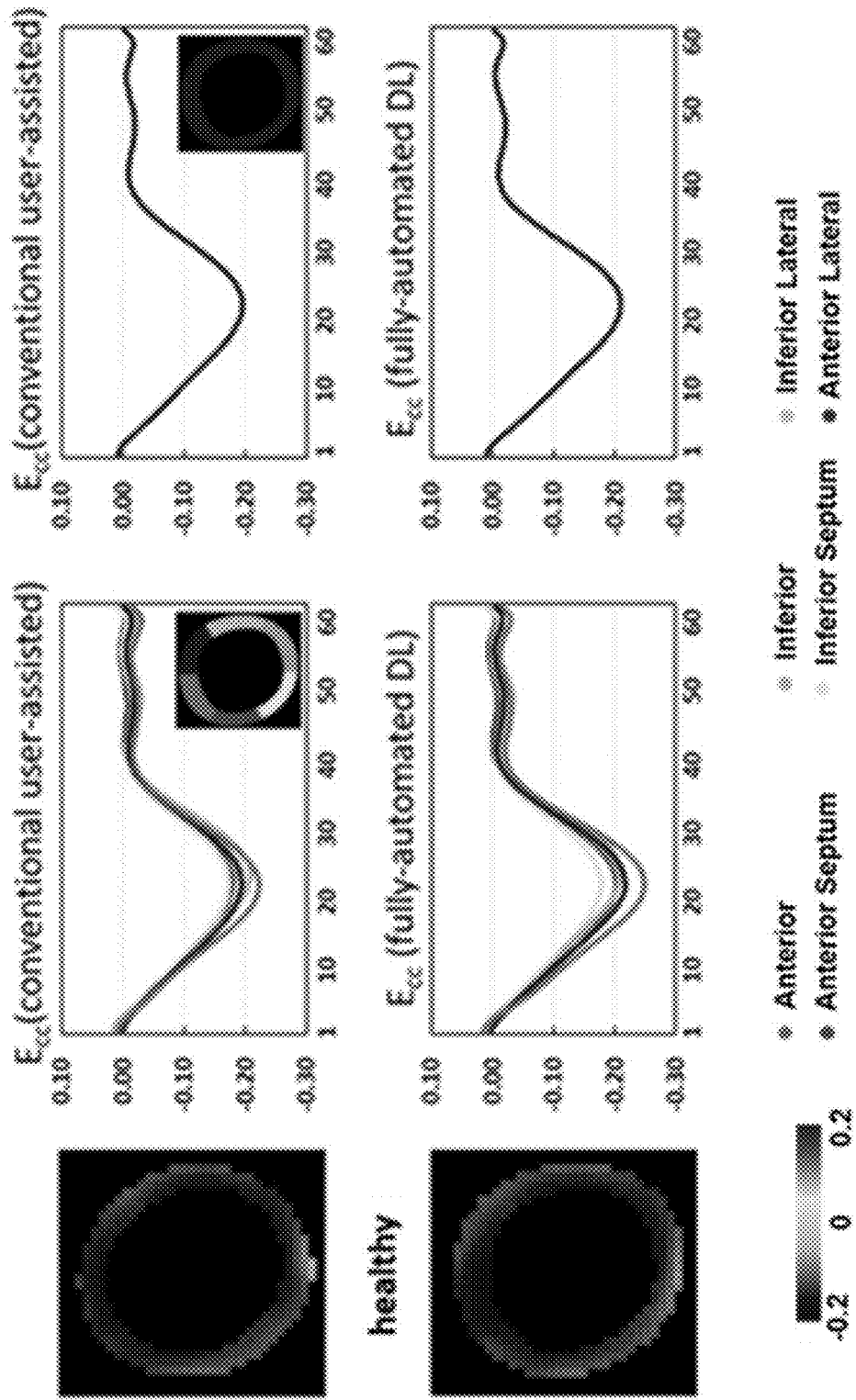
FIGS. 10A-10B illustrate examples of end-systolic circumferential strain maps (left column) and segmental (middle column) and global (right column) circumferential strain-time curves.
Figure 10B:
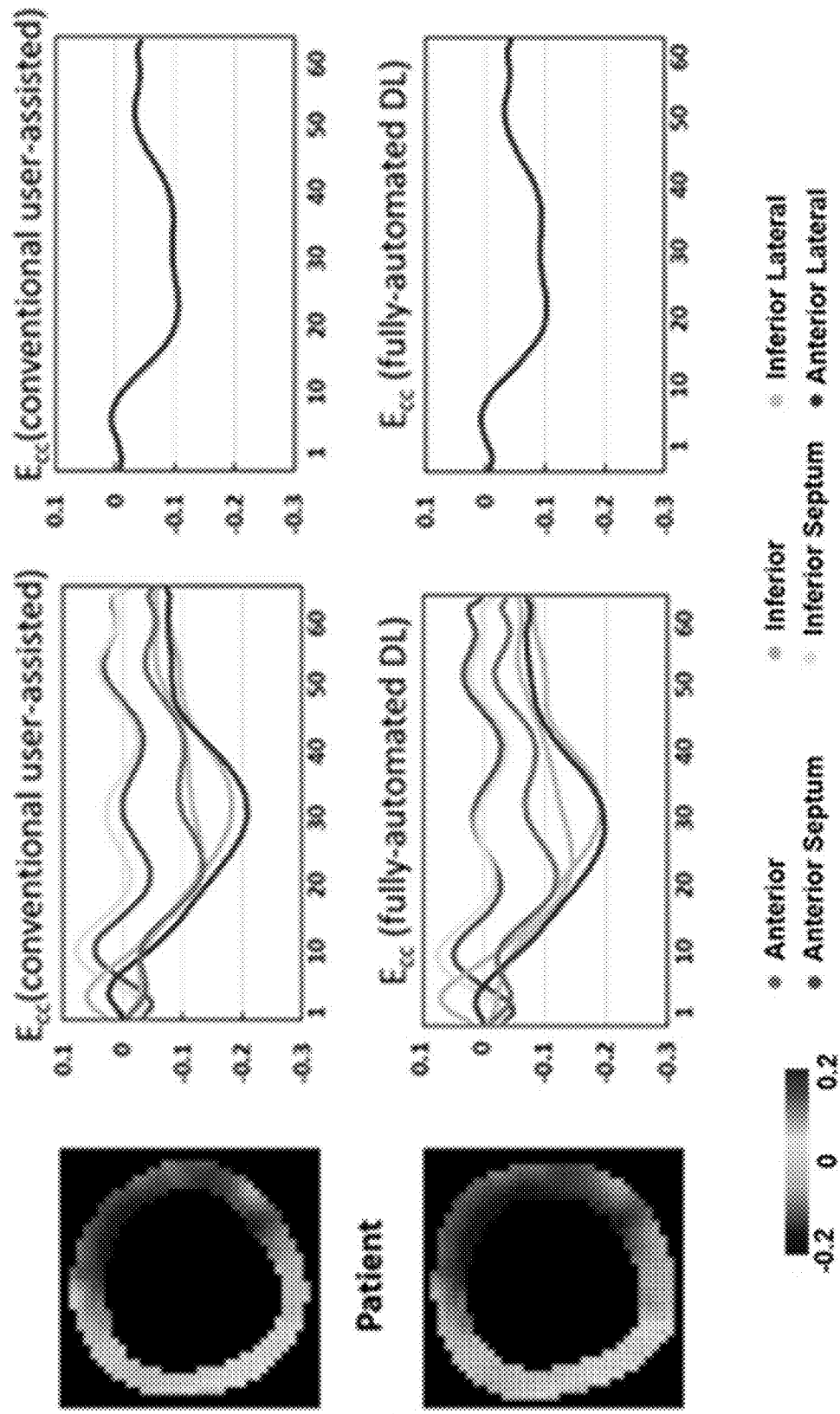
Figure 11A:
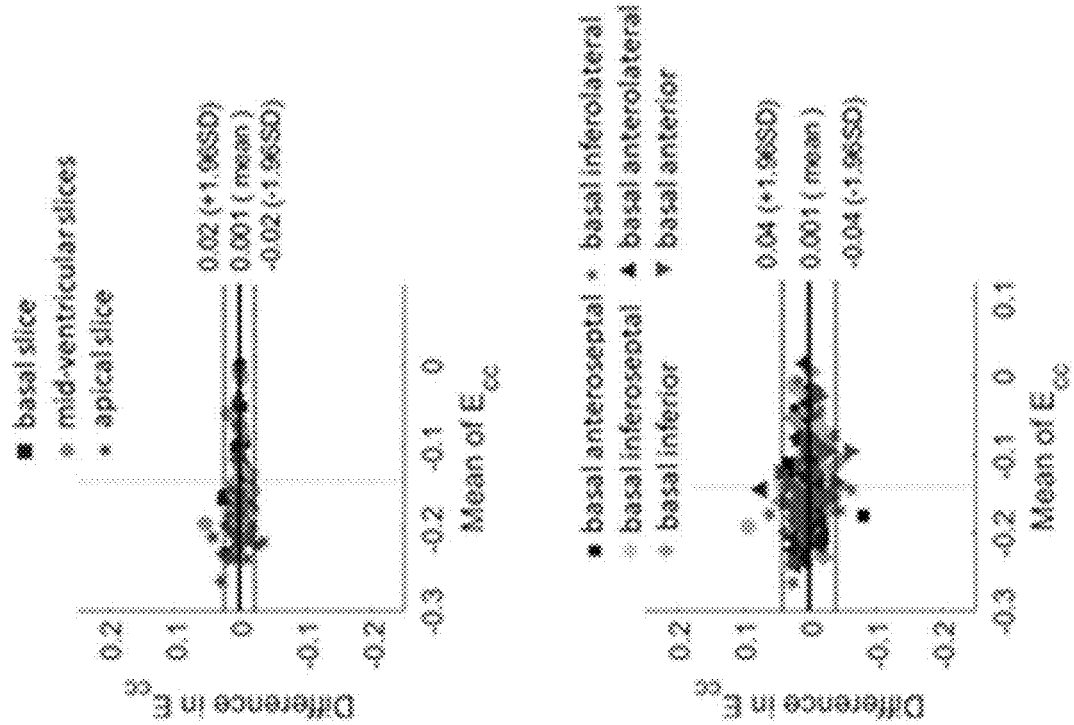
FIGS. 11A-11D illustrate the correlation (left) and Bland-Altman (right) plots for different methods.
Figure 11A:
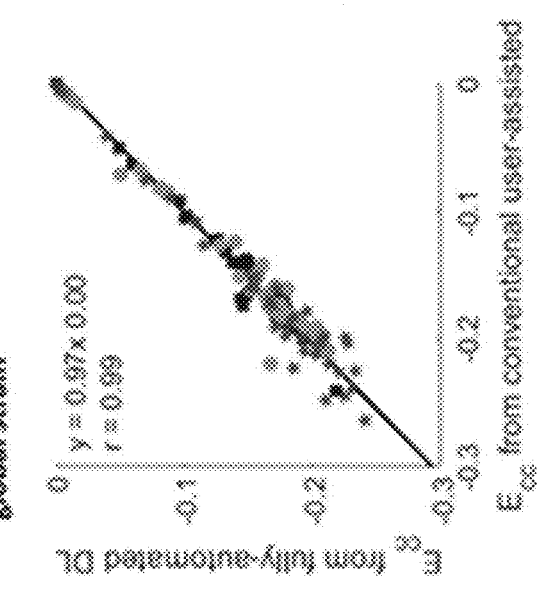
Figure 11B:
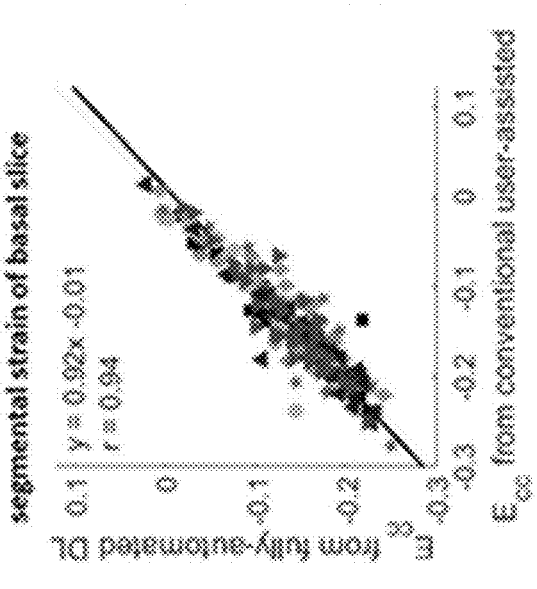
Figure 11C:
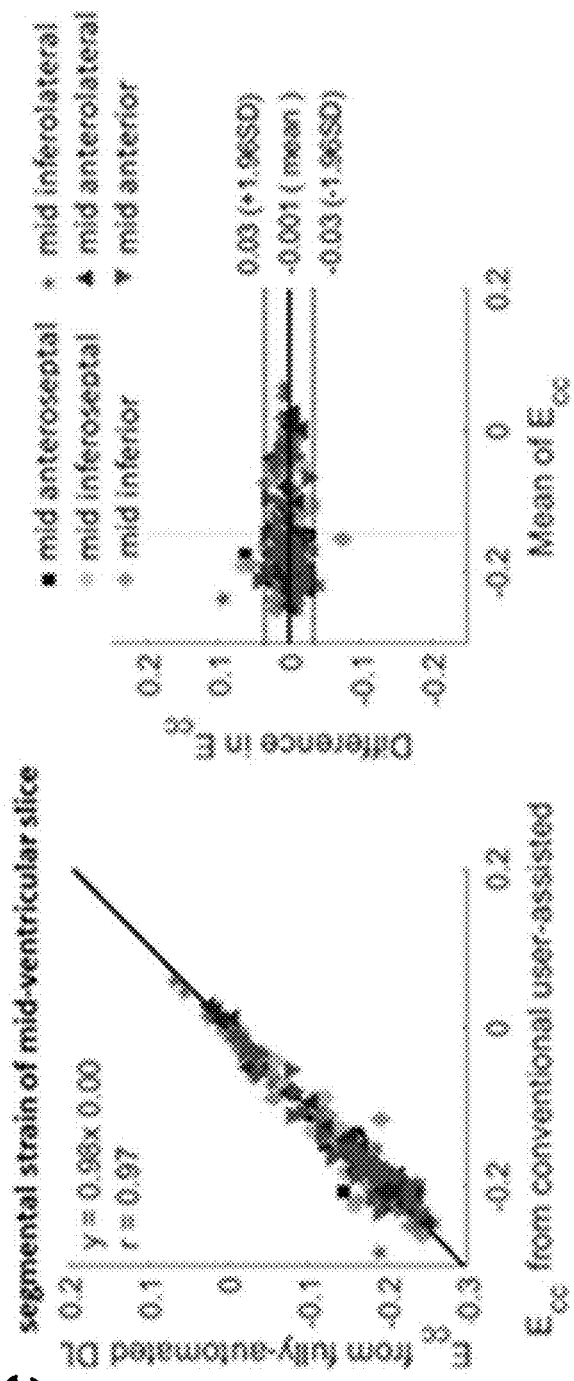
Figure 11D:
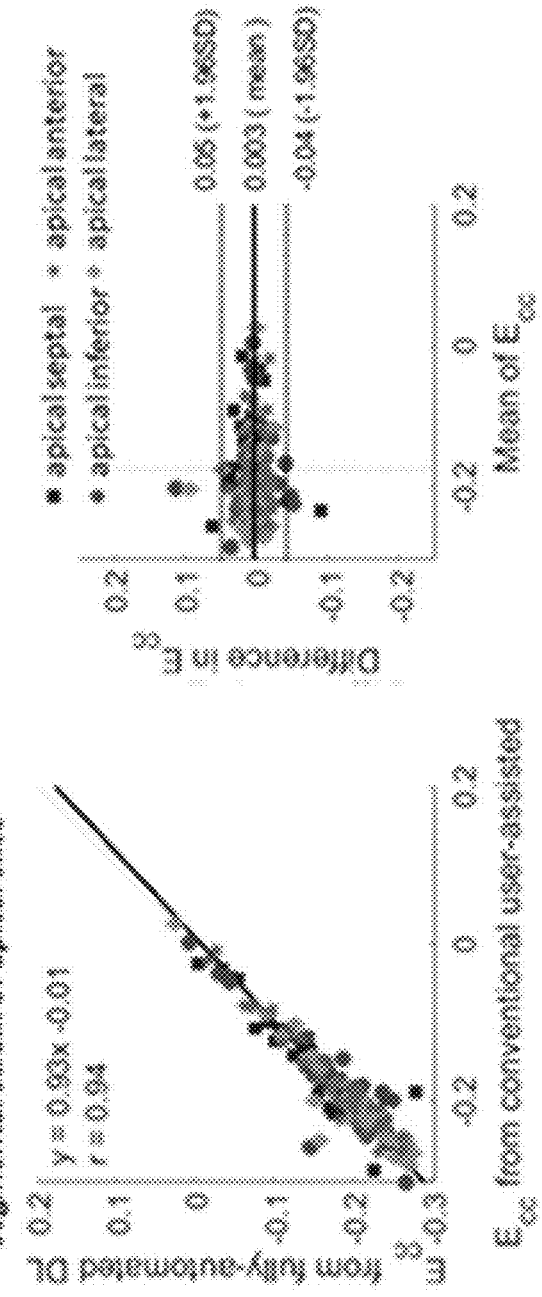

Fully-automated DL methods described herein were used to compute global and segmental circumferential strain for all test data and compared the results with user-assisted DENSE analysis methods[17]. FIGS. 10A and 10B show two examples of end-systolic strain maps, global and segmental strain-time curves computed using the DL-based automated methods and the conventional method for a healthy volunteer and a HF patient with a septal strain defect. Very close agreement between the DL-based and conventional DENSE analysis methods is seen in FIGS. 10A-10D. FIG. 11A shows the Bland-Altman plot and the linear correlation comparing the DL and conventional DENSE analysis methods for end-systolic global circumferential strain. The bias was 0.001 and the limits of agreement were −0.02 and 0.02. For the linear correlation, r=0.97 and the slope was 0.99. A slice-by-slice analysis of segmental strain is provided in FIGS. 11B-11D, and shows very good agreement of segmental end-systolic strain between the fully-automated DL method and the conventional method. The biases were 0.00±0.03 and the limits of agreement were −0.04 to 0.04 for basal segments, −0.03 to 0.03 for mid-ventricular segments, and −0.04 to 0.05 for apical segments. Excellent correlations (r=0.94−0.97, slope=0.92−0.98) were found for all segments of all slices.

FIG. 12 shows the mean±SD of segmental circumferential strain and the variance±SD within each segment at end systole for the mid-ventricular slice of all test data. Two-way ANOVA showed that while there are differences between segments for both mean circumferential strain (p<0.05) and variance of circumferential strain (p<0.05), there are no significant differences between the conventional user-assisted and DL-based fully-automatic methods for mean circumferential strain or the variance of circumferential strain.

The performance of each individual step of an embodiment of the present disclosure was validated, including segmentation, identification of the RV-LV insertion point, and phase unwrapping, and also validated the end-to-end performance of the entire pipeline by showing excellent correlation and agreement of whole-slice and segmental strain with well-established user-assisted semi-automatic methods.

Embodiments of the present disclosure were evaluated for short-axis cine DENSE data from multiple centers and different field strengths (1.5T and 3T). However, it is contemplated that the networks may be trained using long-axis cine DENSE data to compute longitudinal strain and using data from any machine that can provide the DENSE pulse sequence. It is also contemplated that any number of readers can be used to manually contour the data, and the neural networks can be trained or retrained for use with different numbers of readers. Additionally, while the example embodiment described herein was tested using a phase unwrapping neural network trained for one cycle of phase wrap, it should be understood that the methods disclosed herein can be used to perform an arbitrary number of cycles of phase unwrapping (e.g. 2 cycles of phase unwrap). Further, the data augmentation method for phase manipulation can be particularly useful for training with more than one cycle of phase unwrap, as comparatively few real datasets have two cycles of phase wrap. Additionally, it should be understood that the network can be trained on images with respiratory motion, other types of motion, or where the image is off-center, for example by performing further training using images with these qualities. Furthermore, it should be understood that the size of dataset in the present example is intended only as a nonlimiting example and that embodiments of the present disclosure can perform phase unwrapping with an arbitrary amount of training data.

The computerized methods, systems, and products of this disclosure are set forth herein as applied to individual frames of MRI data. This disclosure, however, also encompasses using these phase unwrapping techniques in three dimensional image analyses involving multiple frames of data of higher dimensionality, such as a set of frames of image data gathered over time.

The present study trained CNNs to perform LV segmentation, phase unwrapping, and identification of the anterior RV-LV insertion point for short-axis cine DENSE images, providing for fully-automatic global and segmental DENSE strain analysis with excellent agreement with conventional user-assisted methods. DL-based automatic strain analysis for DENSE may facilitate greater clinical use of DENSE for the assessment of global and segmental strain in heart disease patients.

Figure 13:
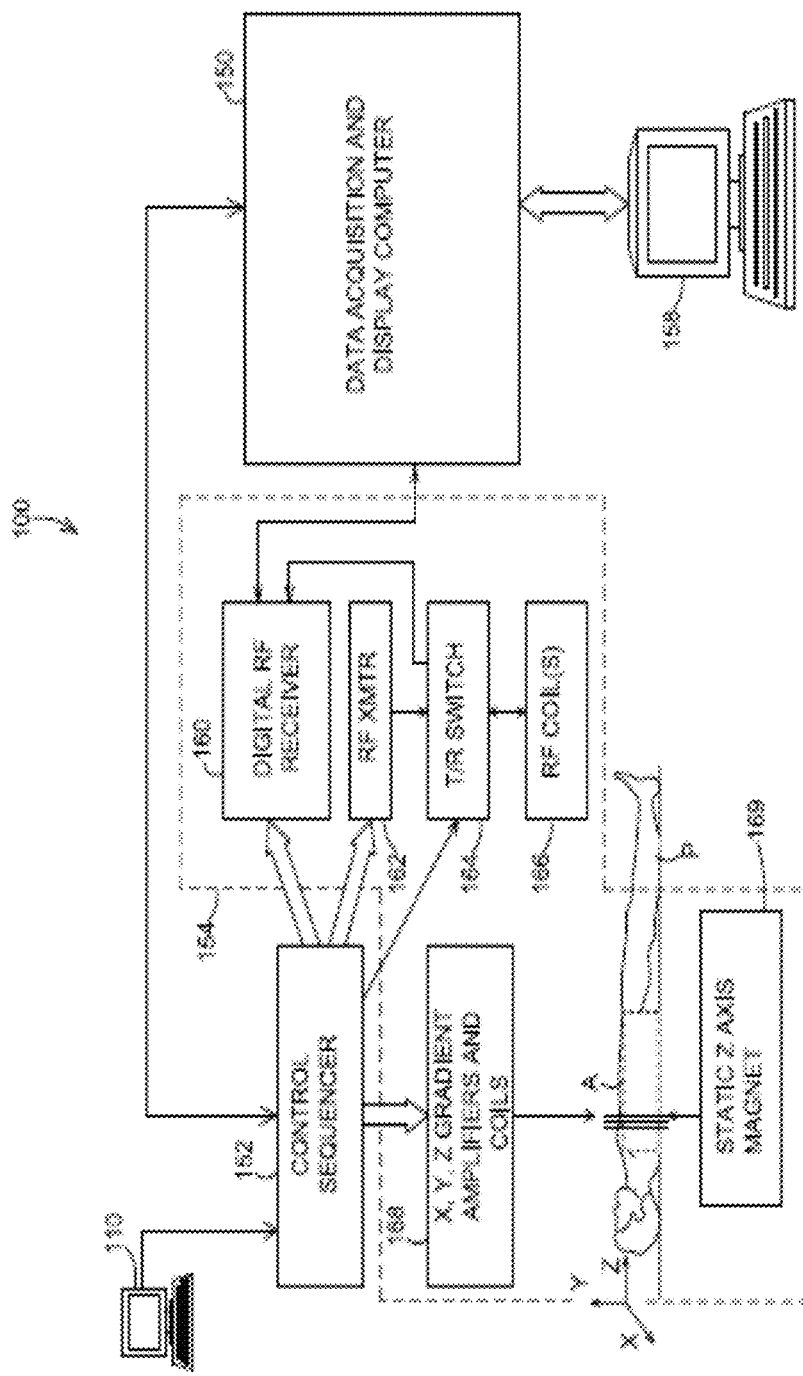
FIG. 13 is a system diagram illustrating an imaging system capable of implementing aspects of the present disclosure in accordance with one or more embodiments.

FIG. 13 is a system diagram is a system diagram illustrating an imaging system capable of implementing aspects of the present disclosure in accordance with one or more embodiments. A magnetic resonance imaging (MRI) system 100 includes a data acquisition and display computer 150 coupled to an operator console 110, an MRI real-time control sequencer 152, and an MRI subsystem 154. The MRI subsystem 154 may include XYZ magnetic gradient coils and associated amplifiers 168, a static Z-axis magnet 169, a digital RF transmitter 162, a digital RF receiver 160, a transmit/receive switch 164, and RF coil(s) 166. The MRI subsystem 154 may be controlled in real time by control sequencer 152 to generate magnetic and radio frequency fields that stimulate magnetic resonance phenomena in a living subject, patient P, to be imaged. A contrast-enhanced image of an area of interest A of the patient P may be shown on display 158. The display 158 may be implemented through a variety of output interfaces, including a monitor, printer, or data storage.

The area of interest "A" corresponds to a region associated with one or more physiological activities in patient "P". The area of interest shown in the example embodiment of FIG. 13 corresponds to a chest region of patient "P", but the area of interest for purposes of implementing aspects of the disclosure presented herein is not limited to the chest area. It should be recognized and appreciated that the area of interest can be one or more of a brain region, heart region, and upper or lower limb regions of the patient "P", for example.

It should be appreciated that any number and type of computer-based medical imaging systems or components, including various types of commercially available medical imaging systems and components, may be used to practice certain aspects of the present disclosure. Systems as described herein with respect to example embodiments are not intended to be specifically limited to magnetic resonance imaging (MRI) implementations or the particular system shown in FIG. 13.

One or more data acquisition or data collection steps as described herein in accordance with one or more embodiments may include acquiring, collecting, receiving, or otherwise obtaining data such as imaging data corresponding to an area of interest. By way of example, data acquisition or collection may include acquiring data via a data acquisition device, receiving data from an on-site or off-site data acquisition device or from another data collection, storage, or processing device. Similarly, data acquisition or data collection devices of a system in accordance with one or more embodiments of the present disclosure may include any device configured to acquire, collect, or otherwise obtain data, or to receive data from a data acquisition device within the system, an independent data acquisition device located on-site or off-site, or another data collection, storage, or processing device.

Figure 14:
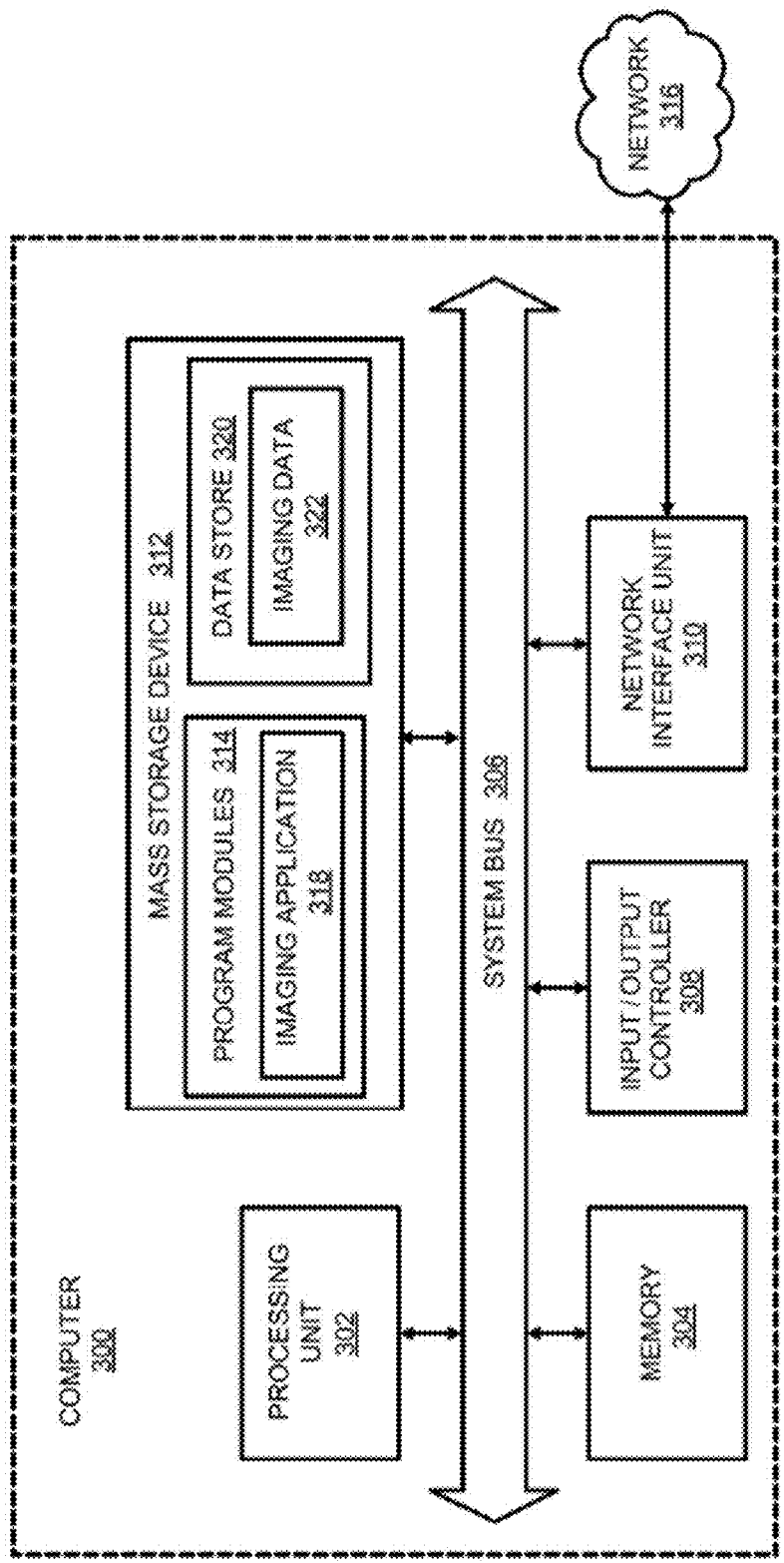
FIG. 14 is a computer architecture diagram showing a computing system capable of implementing aspects of the present disclosure in accordance with one or more embodiments.

FIG. 14 is a computer architecture diagram showing a computing system capable of implementing aspects of the present disclosure in accordance with one or more embodiments described herein. A computer 300 may be configured to perform one or more specific steps of a method and/or specific functions for a system. The computer may be configured to perform one or more functions associated with embodiments illustrated in one or more of FIGS. 1-13. For example, the computer 300 may be configured to perform aspects described herein for implementing the classification and calculation used for phase unwrapping, according to FIGS. 1-13. It should be appreciated that the computer 300 may be implemented within a single computing device or a computing system formed with multiple connected computing devices. The computer 300 may be configured to perform various distributed computing tasks, in which processing and/or storage resources may be distributed among the multiple devices. The data acquisition and display computer 150 and/or operator console 110 of the system shown in FIG. 13 may include one or more components of the computer 300.

As shown, the computer 300 includes a processing unit 302 ("CPU"), a system memory 304, and a system bus 306 that couples the memory 304 to the CPU 302. The computer 300 further includes a mass storage device 312 for storing program modules 314. The program modules 314 may be operable to perform functions associated with one or more embodiments described herein. For example, when executed, the program modules can cause one or more medical imaging devices, localized energy producing devices, and/or computers to perform functions described herein for implementing the data acquisition used in the methods of FIGS. 1A-1B. The program modules 314 may include an imaging application 318 for performing data acquisition and/or processing functions as described herein, for example to acquire and/or process image data corresponding to magnetic resonance imaging of an area of interest. The computer 300 can include a data store 320 for storing data that may include imaging-related data 322 such as acquired data from the implementation of magnetic resonance imaging pulse sequences in accordance with various embodiments of the present disclosure.

The mass storage device 312 is connected to the CPU 302 through a mass storage controller (not shown) connected to the bus 306. The mass storage device 312 and its associated computer-storage media provide non-volatile storage for the computer 300. Although the description of computer-storage media contained herein refers to a mass storage device, such as a hard disk, it should be appreciated by those skilled in the art that computer-storage media can be any available computer storage media that can be accessed by the computer 300.

CONCLUSION

The specific configurations, choice of materials and the size and shape of various elements can be varied according to particular design specifications or constraints requiring a system or method constructed according to the principles of the disclosed technology. Such changes are intended to be embraced within the scope of the disclosed technology. The presently disclosed embodiments, therefore, are considered in all respects to be illustrative and not restrictive. The patentable scope of certain embodiments of the present disclosure is indicated by the appended claims, rather than the foregoing description.

REFERENCES

[1] Szymanski, C., Levy, F. & Tribouilloy, C. Should LVEF be replaced by global longitudinal strain? *Heart* 100, 1655 LP-1656 (2014).

[2] Aletras, A. H., Ding, S., Balaban, R. S. & Wen, H. DENSE: displacement encoding with stimulated echoes in cardiac functional MRI. *J. Magn. Reson.* 137, 247-252 (1999).

[3] Kim, D., Gilson, W. D., Kramer, C. M. & Epstein, F. H. Myocardial tissue tracking with two-dimensional cine displacement-encoded MR imaging: development and initial evaluation. *Radiology* 230, 862-871 (2004).

[4] Zhong, X., Spottiswoode, B. S., Meyer, C. H., Kramer, C. M. & Epstein, F. H. Imaging three-dimensional myocardial mechanics using navigator-gated volumetric spiral cine DENSE MRI. *Magn. Reson. Med.* 64, 1089-1097 (2010).

[5] Spottiswoode, B. S. et al. Tracking myocardial motion from cine DENSE images using spatiotemporal phase unwrapping and temporal fitting. *IEEE Trans. Med. Imaging* 26, 15-30 (2007).

[6] Young, A. A., Li, B., Kirton, R. S. & Cowan, B. R. Generalized spatiotemporal myocardial strain analysis for DENSE and SPAMM imaging. *Magn. Reson. Med.* 67, 1590-1599 (2012).

[7] Lin, K. et al. Reproducibility of cine displacement encoding with stimulated echoes (DENSE) in human subjects. *Magn. Reson. Imaging* 35, 148-153 (2017).

[8] Spottiswoode, B. S. et al. Motion-guided segmentation for cine DENSE MRI. *Med. Image Anal.* 13, 105-115 (2009).

[9] Mangion, K. et al. Circumferential Strain Predicts Major Adverse Cardiovascular Events Following an Acute ST-Segment-Elevation Myocardial Infarction. *Radiology* 290, 329-337 (2019).

[10] Bilchick, K. C. et al. CMR DENSE and the Seattle Heart Failure Model Inform Survival and Arrhythmia Risk After CRT. *JACC. Cardiovasc. Imaging* 13, 924-936 (2020).

[11] Jing, L. et al. Cardiac remodeling and dysfunction in childhood obesity: a cardiovascular magnetic resonance study. *J. Cardiovasc. Magn. Reson.* 18, 28 (2016).

12] Ernande, L. et al. Systolic myocardial dysfunction in patients with type 2 diabetes mellitus: Identification at MR imaging with cine displacement encoding with stimulated echoes. *Radiology* 265, 402-409 (2012).

[13] Chen, X., Salerno, M., Yang, Y. & Epstein, F. H. Motion-compensated compressed sensing for dynamic contrast-enhanced MRI using regional spatiotemporal sparsity and region tracking: block low-rank sparsity with motion-guidance (BLOSM). *Magn. Reson. Med.* 72, 1028-1038 (2014).

[14] Chen, X. et al. Accelerated two-dimensional cine DENSE cardiovascular magnetic resonance using compressed sensing and parallel imaging. *J. Cardiovasc. Magn. Reson.* 18, 38 (2016).

[15] Tayal, U. et al. The feasibility of a novel limited field of view spiral cine DENSE sequence to assess myocardial strain in dilated cardiomyopathy. *Magn. Reson. Mater. Physics, Biol. Med.* 32, 317-329 (2019).

[16] Cerqueira, M. D. et al. Standardized myocardial segmentation and nomenclature for tomographic imaging of the heart. *J. Cardiovasc. Magn. Reson.* 4, 203-210 (2002).

[17] Gilliam, A. D., Suever, J. D. DENSEanalysis: Cine DENSE Processing Software. https://github.com/dense-analysis/denseanalysis.

[18] D'Errico, J. Surface Fitting using gridfit. *MATLAB Central File Exchange* vol. 1 1-6 http://uk.mathworks-.com/matlabcentral/fileexchange/8998-surface-fitting-using-gridfit (2020).

[19] Bal, W. et al. Automated cardiovascular magnetic resonance image analysis with fully convolutional networks. *J. Cardiovasc. Magn. Reson.* 20, 65 (2018).

[20] Puyol-Anton, E. et al. Fully automated myocardial strain estimation from cine MRI using convolutional neural networks. in 2018 *IEEE 15th International Symposium on Biomedical Imaging, ISBI* 2018 vols 2018-April 1139-1143 (IEEE Computer Society, 2018).

[21] Tan, L. K., McLaughlin, R. A., Lim, E., Abdul Aziz, Y. F. & Liew, Y. M. Fully automated segmentation of the left ventricle in cine cardiac MRI using neural network regression. *J. Magn. Reson. Imaging* 48, 140-152 (2018).

[22] Zheng, Q., Delingette, H., Duchateau, N. & Ayache, N. 3-D Consistent and Robust Segmentation of Cardiac Images by Deep Learning With Spatial Propagation. *IEEE Trans. Med. Imaging* 37, 2137-2148 (2018).

[23] Bratt, A. et al. Machine learning derived segmentation of phase velocity encoded cardiovascular magnetic resonance for fully automated aortic flow quantification. *J. Cardiovasc. Magn. Reson.* 21, 1 (2019).

[24] Duan, J. et al. Automatic 3D Bi-Ventricular Segmentation of Cardiac Images by a Shape-Refined Multi-Task Deep Learning Approach. *IEEE Trans. Med. Imaging* 38, 2151-2164 (2019).

[25] Fahmy, A. S., El-Rewaidy, H., Nezafat, M., Nakamori, S. & Nezafat, R. Automated analysis of cardiovascular magnetic resonance myocardial native T1 mapping images using fully convolutional neural networks. *J. Cardiovasc. Magn. Reson.* 21, 7 (2019).

[26] Tao, Q. et al. Deep Learning-based Method for Fully Automatic Quantification of Left Ventricle Function from Cine MR Images: A Multivendor, Multicenter Study. *Radiology* 290, 81-88 (2019).

[27] Fahmy, A. S. et al. Three-dimensional Deep Convolutional Neural Networks for Automated Myocardial Scar Quantification in Hypertrophic Cardiomyopathy: A Multicenter Multivendor Study. *Radiology* 294, 52-60 (2019).

[28] Ruijsink, B. et al. Fully Automated, Quality-Controlled Cardiac Analysis From CMR: Validation and Large-Scale Application to Characterize Cardiac Function. *JACC Cardiovasc. Imaging* 13, 684-695 (2020).

[29] Ferdian, E. et al. Fully Automated Myocardial Strain Estimation from Cardiovascular MRI-tagged Images Using a Deep Learning Framework in the UK Biobank. *Radiol. Cardiothorac. Imaging* 2, e190032 (2020).

[30] Zhong, X., Helm, P. A. & Epstein, F. H. Balanced multipoint displacement encoding for DENSE MRI. *Magn. Reson. Med.* 61, 981-988 (2009).

[31] Verzhbinsky, I. A. et al. Estimating Aggregate Cardiomyocyte Strain Using In Vivo Diffusion and Displacement Encoded MRI. *IEEE Trans. Med. Imaging* 39, 656-667 (2020).

[32] Ronneberger, O., Fischer, P. & Brox, T. U-Net: Convolutional Networks for Biomedical Image Segmentation. in *MICCAI* (2015).

[33] Feng, X., Qing, K., Tustison, N. J., Meyer, C. H. & Chen, Q. Deep convolutional neural network for segmentation of thoracic organs-at-risk using cropped 3D images. *Med. Phys.* 46, 2169-2180 (2019).

[34] Feng, X., Kramer, Chirstopher M., Meyer, C. H. View-independent cardiac MRI segmentation with rotation-based training and testing augmentation using a dilated convolutional neural network. in *ISMRM 27th Annual Meeting* (2019).

[35] Spoorthi, G. E., Gorthi, S. & Gorthi, R. K. PhaseNet: A Deep Convolutional Neural Network for Two-Dimensional Phase Unwrapping. *IEEE Signal Process. Lett.* 26, 54-58 (2019).

[36] Auger, D. A., Cai, X., Sun, Ch., Epstein, F. H. Improved phase unwrapping algorithm for automatic cine DENSE strain analysis using phase predictions and region growing. in *SMRT 27th Annual Meeting* (2018).

[37] Abadi, M. et al. TensorFlow: Large-Scale Machine Learning on Heterogeneous Distributed Systems. *CoRR* abs/1603.0, (2016).

[38] Zou, K. H. et al. Statistical validation of image segmentation quality based on a spatial overlap index. *Acad. Radiol.* 11, 178-189 (2004).

[39] Bilchick, K. C. et al. Impact of mechanical activation, scar, and electrical timing on cardiac resynchronization therapy response and clinical outcomes. *J. Am. Coll. Cardiol.* 63, 1657-1666 (2014).

[40] Lee, A. T., Bruce Pike, G. & Pelc, N. J. Three-Point Phase-Contrast Velocity Measurements with Increased Velocity-to-Noise Ratio. *Magn. Reson. Med.* 33,122-126 (1995).

[41] Hammouda, K. et al. A New Framework for Performing Cardiac Strain Analysis from Cine MRI Imaging in Mice. *Sci. Rep.* 10, 7725 (2020).

[42] Wang, K., Li, Y., Kemao, Q., Di, J. & Zhao, J. One-step robust deep learning phase unwrapping. *Opt. Express* 27, 15100-15115 (2019).

[43] Dardikman-Yoffe, G. et al. PhUn-Net: ready-to-use neural network for unwrapping quantitative phase images of biological cells. *Biomed. Opt. Express* 11, 1107-1121 (2020).

[44] Yin, W. et al. Temporal phase unwrapping using deep learning. *Sci. Rep.* 9, 20175 (2019).

[45] Zhang, J., Tian, X., Shao, J., Luo, H. & Liang, R. Phase unwrapping in optical metrology via denoised and convolutional segmentation networks. *Opt. Express* 27, 14903-14912 (2019).

[46] Zhang, T. et al. Rapid and robust two-dimensional phase unwrapping via deep learning. *Opt. Express* 27, 23173-23185 (2019).

[47] Suever, J. D. et al. Simplified post processing of cine DENSE cardiovascular magnetic resonance for quantification of cardiac mechanics. *J. Cardiovasc. Magn. Reson.* 16, 94 (2014).

What is claimed is:

1. A method of strain analysis of a cardiac region of interest of a subject from displacement encoded magnetic resonance image (MRI) data, the method comprising:
    acquiring displacement encoded MRI data corresponding to the cardiac region of interest of the subject;
    generating a phase image for each frame of the displacement encoded MRI data, wherein the phase image comprises potentially phase-wrapped measured phase values corresponding to pixels of the frame;
    training a convolutional neural network (CNN) to compute a wrapping label map for the phase image, wherein the wrapping label map comprises a number of phase wrap cycles present at each pixel in the phase image;
    computing, by the trained CNN, the wrapping label map;
    computing an unwrapped phase image by adding a respective phase correction to each of the potentially phase-wrapped measured phase values of the phase image, wherein the phase correction is based on the number of phase wrap cycles present at each pixel; and
    computing myocardial strain using the unwrapped phase image for strain analysis of the subject.

2. The method of claim 1, wherein the strain analysis comprises quantification of global and segmental strain associated with the heart of the subject.

3. The method of claim 1, wherein the displacement encoded MRI data corresponds to displacement encoded stimulated echo (DENSE) cine frames of MRI image data.

4. The method of claim 1, wherein a U-Net structured CNN is used to compute the wrapping label map.

5. The method of claim 1, further comprising at least one additional CNN configured for epicardial and endocardial segmentation, and wherein the at least one additional CNN assigns one of three classes to each pixel, wherein the three classes comprise the blood pool, the myocardium, and the background.

6. The method of claim 1, wherein computing the wrapping label map comprises labeling each pixel as belonging to one of three classes, the classes comprising no-wrap, $-2\pi$ wrapped, and $+2\pi$ wrapped.

7. The method of claim 6, further comprising displaying a visual representation of the phase image according to the respective class and label.

8. The method of claim 1, wherein at least one trained CNN is trained at least in part from augmented test data from previously verified test images produced by phase unwrapping the previously verified test image, multiplying a phase unwrapped verified test image by a constant, and phase wrapping a product test image within a range of $-\pi$ to $+\pi$ to generate a new wrap test image.

9. The method of claim 1, further comprising using at least one additional CNN to:
    (a) identify the left-ventricular (LV) epicardial and endocardial borders; and
    (b) identify the interior right ventricular-LV insertion point.

10. The method of claim 1, further comprising using at least one additional CNN to generate:
(a) segmentation of the LV myocardium;
(b) identification of the anterior right-ventricular (RV) insertion point into the LV; and
(c) an unwrapped phase image by unwrapping of the potentially-wrapped displacement encoded phase values of the myocardium.

11. The method of claim 10, further comprising:
(d) computing the spatiotemporal displacement field of the unwrapped phase image.

12. The method of claim 1, wherein:
the potentially phase-wrapped measured phase values correspond to pixel (i, j) of the frame;
the wrapping label map comprises values of respective wrapping constants $k_{ij}$ for each pixel (i, j) in the phase image;
the respective phase correction for each pixel (i, j) is computed by multiplying each value $k_{ij}$ by $2\pi$; and
the unwrapped phase image is computed by adding the phase correction for each pixel (i, j) to each of the potentially phase-wrapped measured phase values of the phase image.

13. The method of claim 1, wherein the frames of the displacement encoded MRI data comprise image frames having displacement encoded data generated with multiple cycles of phase wrapping.

14. The method of claim 13, further comprising using the trained CNN to estimate the number of cycles of wrapping corresponding to the phase image during displacement encoding that produced the displacement encoded MRI data.

15. The method of claim 1, further comprising converting the unwrapped phase image to a respective displacement array.

16. A system, comprising:
a data acquisition device configured to acquire displacement encoded magnetic resonance image (MRI) data corresponding to a cardiac region of interest of a subject;
a computer-implemented convolutional neural network (CNN);
one or more processors coupled to the data acquisition device and the CNN and configured to cause the system to perform functions that comprise:
generating a phase image for each frame of the displacement encoded MRI data, wherein the phase image comprises potentially phase-wrapped measured phase values corresponding to pixels of the frame;
training a convolutional neural network (CNN) to compute a wrapping label map for the phase image, wherein the wrapping label map comprises a respective number of phase wrap cycles present at each pixel in the phase image;
computing, by the trained CNN, the wrapping label map;
computing an unwrapped phase image by adding a respective phase correction to each of the potentially phase-wrapped measured phase values of the phase image, wherein the phase correction is based on the number of phase wrap cycles present at each pixel; and
computing myocardial strain using the unwrapped phase image for strain analysis of the subject.

17. A non-transitory computer-readable medium storing instructions which, when executed by one or more processors, cause one or more computing devices to perform functions for strain analysis of a cardiac region of interest of a subject from displacement encoded magnetic resonance image (MRI) data, and wherein the performed functions comprise:
acquiring displacement encoded MRI data corresponding to the cardiac region of interest of the subject;
generating a phase image for each frame of the displacement encoded MRI data, wherein the phase image comprises potentially phase-wrapped measured phase values corresponding to pixels of the frame;
training a convolutional neural network (CNN) to compute a wrapping label map for the phase image, wherein the wrapping label map comprises a respective number of phase wrap cycles present at each pixel in the phase image;
computing, by the trained CNN, the wrapping label map;
computing an unwrapped phase image by adding a respective phase correction to each of the potentially phase-wrapped measured phase values of the phase image, wherein the phase correction is based on the number of phase wrap cycles present at each pixel; and
computing myocardial strain using the unwrapped phase image for strain analysis of the subject.

* * * * *